| United States Patent [19] | [11] Patent Number: 4,721,669 |
| Barton | [45] Date of Patent: Jan. 26, 1988 |

[54] CHEMICAL PROBES FOR LEFT-HANDED DNA AND CHIRAL METAL COMPLEXES AS Z-SPECIFIC ANTI-TUMOR AGENTS

[75] Inventor: Jacqueline K. Barton, New York, N.Y.

[73] Assignee: The Trustees of Columbia University in the City of New York, New York, N.Y.

[21] Appl. No.: 693,023

[22] Filed: Jan. 18, 1985

[51] Int. Cl.$^4$ .................. C12Q 1/68; C07H 21/00; C07D 471/04; A61K 33/24
[52] U.S. Cl. .................................. 435/6; 935/78; 546/88; 536/27; 424/131; 204/157.72
[58] Field of Search ............... 546/4, 10, 88; 536/22, 536/27; 556/136, 138; 424/1.1, 9, 131, 149; 435/6; 935/77, 78; 204/157.71, 157.72

[56] References Cited

U.S. PATENT DOCUMENTS 4,395,486 7/1983 Wilson et al. ............... 436/508 X
4,547,569 10/1985 Letsinger et al. ............. 536/29

OTHER PUBLICATIONS

Barton, J. K. et al, *J. Am. Chem. Soc.*, vol. 106, No. 8, 1984, pp. 2466–2468.
Barton, J. K. et al, *J. Am. Chem. Soc.*, vol. 106, No. 7, 1984, pp. 2172–2176.
Barton, J. K. et al, *Proc. Natl. Acad. Sci. USA*, vol. 81, Apr. 1984, pp. 1961–1965.
Barton, J. K. et al, *J. Am. Chem. Soc.*, vol. 104, No. 18, 1982, pp. 4967–4969.
Yamagishi, A., *J. Chem. Soc., Chem. Commun.*, vol. 10, 1983, pp. 572–573.
Chang, C. H. et al, *Biochemistry*, vol. 21, 1982, pp. 6332–6334.
Chang, C. H. et al, *Biochemistry*, vol. 23, 1984, pp. 2268–2274.
Pommier, Y. et al, *Biochemistry*, vol. 23, No. 14, 1984, pp. 3194–3201.
Pope, L. M. et al, *J. Biol. Chem.*, vol. 257, Oct. 1982, pp. 12121–12128.

*Primary Examiner*—Esther M. Kepplinger
*Assistant Examiner*—Jeremy Jay
*Attorney, Agent, or Firm*—John P. White

[57] ABSTRACT

This invention concerns a coordination complex and salts and optically resolved enantiomers thereof, of the formula $(R)_3$—M, wherein R comprises 1,10-phenanthroline or a substituted derivative thereof, M comprises a suitable transition metal, e.g. ruthenium(II) or cobalt(III), and R is bonded by M by a coordination bond.

The complexes of this invention are useful in methods for labeling, nicking and cleaving DNA. The lambda enantiomer of complexes of this invention is useful in methods for specifically labeling, detecting, nicking and cleaving Z-DNA.

The complexes may also be used in a method for killing tumor cells and may be combined with a pharmaceutically acceptable carrier to form a pharmaceutical composition for the treatment of tumor cells in a subject. The invention further concerns methods for treating a subject afflicted with tumor cells.

10 Claims, 20 Drawing Figures

Fig. 3
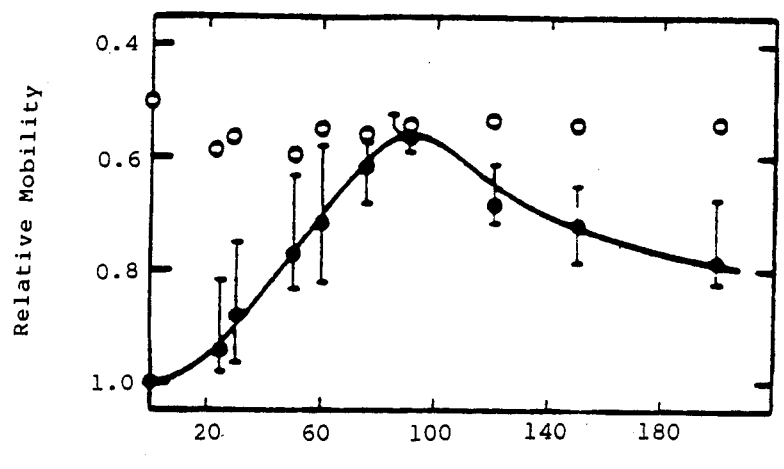
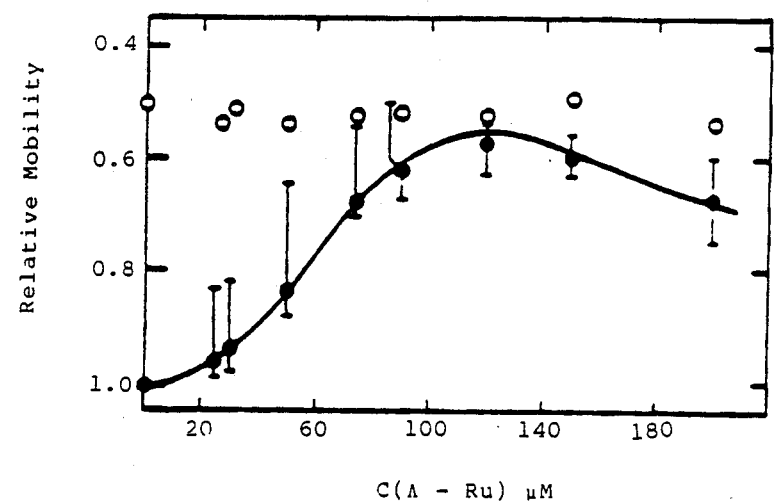

Fig. 9B
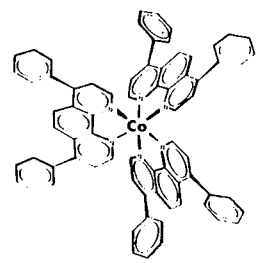
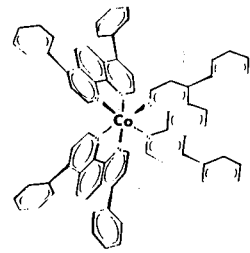
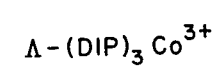
$\Lambda-(DIP)_3 Co^{3+}$
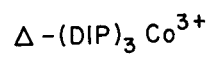
$\Delta-(DIP)_3 Co^{3+}$
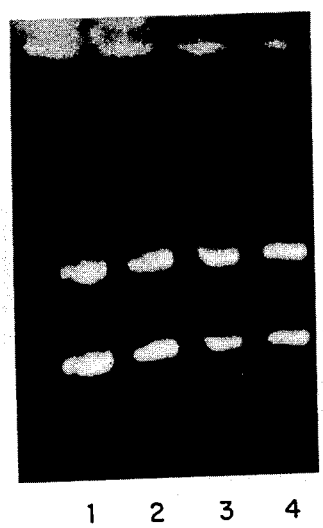
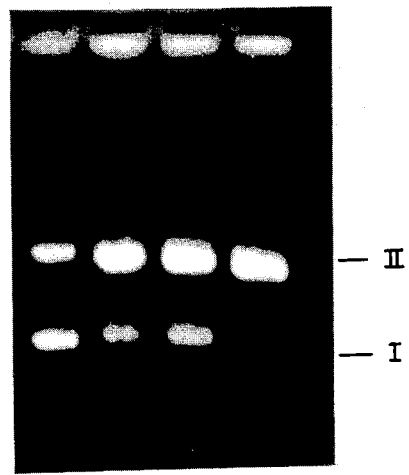
— II
— I
1  2  3  4        5  6  7  8

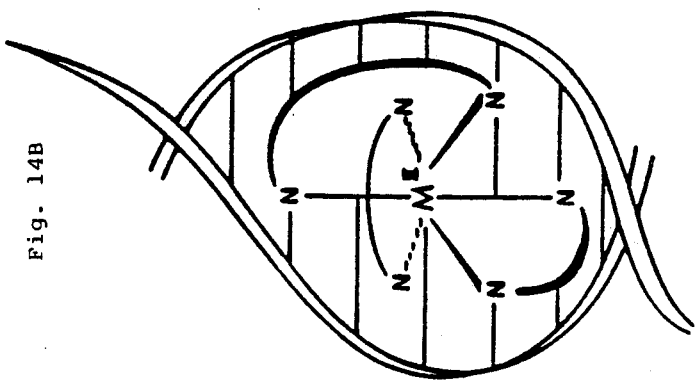
Fig. 14B    Delta
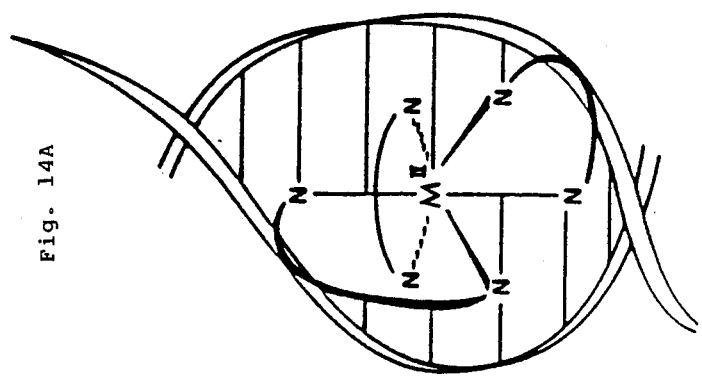
Fig. 14A    Lambda

CHEMICAL PROBES FOR LEFT-HANDED DNA AND CHIRAL METAL COMPLEXES AS Z-SPECIFIC ANTI-TUMOR AGENTS

This invention was made with government support under grant numbers GM 32203 and GM 33309 from the National Institutes of Health, U.S. Department of Health and Human Services, and grant number CHE-83-51017 from the National Science Foundation. The government has certain rights in this invention.

BACKGROUND OF THE INVENTION

Much of the information set forth herein has been published. See Barton, J. K. et al., J. Am. Chem. Soc., 1984, 106: 2172–2176 (Apr. 6, 1984); Barton, J. K. and Raphael, A., J. Am. Chem. Soc., 1984, 106: 2466–2468 (Apr. 18, 1984); Barton, J. K. et al., Proc. Natl. Acad. Sci. USA, 1984, 81:1961–1965 (Apr. 27, 1984); and Barton, J. K., J. Biom. Structure and Dynam., 1983, 1: 621–632 (Jan. 18, 1984). The above-mentioned papers were distributed by the respective publishers on the dates provided in parentheses.

Throughout this application various publications are referenced by arabic numerals within parentheses. Full citations for these publications may be found at the end of the specification immediately preceding the claims. The disclosures of these publications in their entireties are hereby incorporated by reference into this application in order to more fully describe the state of the art to which this invention pertains.

The binding of heterocyclic compounds to DNA by intercalation, where the planar aromatic cation stacks between adjacent base pairs of the duplex (1), has been the subjected of considerable investigation (2–4).

Intercalative drugs can be strongly mutagenic, and some, as adriamycin and daunomycin, serve as potent chemotherapeutic agents (5). The small intercalators such as ethidium or proflavine in addition provide useful chemical probes of nucleic acid structure (6). Metallointercalators have been particularly useful in probing DNA structure and the intercalation process itself, because the ligands or metal may be varied in an easily controlled manner to facilitate the individual application (7).

The aromatic chromophore of the intercalative cation can provide a sensitive handle to monitor the conformation and flexibility of the helix. Many intercalators show antibacterial or anticancer activity and, because the inserted residue often resembles a base pair in shape and thickness, intercalators are commonly frame shaft mutagens. (3) Intercalation appears to require, simply, a planar heterocyclic residue, (4) and in fact cationic metal complexes which contain aromatic ligands bind to DNA by intercalation as well. (5) Platinum intercalators have uniquely provided electron dense probes for x-ray diffraction experiments. (6) Moreover the metallointercalation reagents have offered particular experimental flexibility in that both the metal and accessory ligands may be varied for individual applications. Comparisons of the binding of the intercalative 2,2'-bipyridylplatinum(II) reagent with the analogous nonintercalating bis(pyridine)platinum(II) species by fiber X-ray diffraction methods, for example, demonstrated quite simply the requirement for ligand planarity in the intercalation process (8).

The original studies of metallointercalators centered on square-planar platinum(II) complexes containing aromatic terpyridyl or phenanthroline ligands (9), and single-crystal studies of terpyridylplatinum(II) species stacked with nucleotides showed the platinum complex to insert almost fully between the base pairs (10, 11). More recently the reagent methidiumpropyl-Fe(II)EDTA, which contains a redox-active metal center tethered to an organic intercalator, has been applied in "footprinting" experiments to determine the sequence specificities of small drugs bound to DNA (12). Bis(phenanthroline)-cuprous ion (13) has similarly been employed in DNA cleavage experiments (14), and this reagent also presumably binds initially to the DNA by intercalation. (3,5,6,8-tetramethyl-1,10-phenanthroline)$_3$Ru(II) has been reported and its use against influenza virus, fungus, yeast and leukemia investigated (98). The ability of the tris tetramethyl complex to bind to or cleave DNA has not been reported. Furthermore, enantiomers of that complex have not been separated and their respective properties compared.

Reagents of high specificity and even stereoselectivity would be desirable in the design both of potent drugs and of structural probes. For the chiral complex (phen)$_3$Zn$^{2+}$ (phen=1,10-phenanthroline) an enantiomeric preference in binding to B-DNA has been observed (15). As for the tetrahedral (phen)$_2$Cu$^+$ complex, and in contrast to the square-planar platinum intercalators, the octahedral coordination in the tris(phenanthroline) metal cations can permit a partial insertion of only one coordinated ligand. Thus while one ligand is stacked between base pairs, the remaining nonintercalated phenanthroline ligands should be available to direct the enantiomeric selection.

The left-handed DNA helix has received considerable attention since the original crystallographic study of the Z-DNA fragment [d(CpG)]$_6$ (16). Solution conditions that include high ionic strength (17), hydrophobic solvents (18), the presence of certain trivalent cations (19), or covalent modification with bulky alkylating agents (19–23) all facilitate the transition of a right-handed double helix into a left-handed form. This striking conformational transition was first observed for poly[d(G-C)] (17). More recently, the alternating purine-pyrimidine sequence [d(G-T)]$_n$·[d(C-A)]$_n$ has been shown to form Z-helices as well (24, 25). Methylation of cytosine residues at carbon-5 lends stability to Z-form DNA (19, 26) and, under physiological conditions, transitions to a left-handed structure can occur to relieve the torsional strain in underwound negatively supercoiled DNA (27–29). These latter findings suggest mechanisms for left-handed DNA formation in the cell, where such structures could be important in controlling gene expression. Negatively supercoiled simian virus 40 DNA, for example, has been found to contain potentially Z-DNA-forming alternate purine-pyrimidine regions within transcriptional enhancer sequences (30).

To explore any biological role for left-handed DNA, sensitive and selective probes are required. Assays of superhelix unwinding, NMR experiments and circular dichroism have been used in detecting Z-DNA. These methods, however, are indirect, do not assay for helix handedness, and require large quantitites of material. More recently antibodies to Z-DNA have been elicited. The antibodies provide a more sensitive means of detection. Z-DNA appears to be a strong immunogen. Anti-Z-DNA antibodies have been elicited with both brominated poly[d(G-C)] (31) and poly[d(G-C)] modified with diethylenetriamineplatinum(II) (32) as antigens. The structures of Z-DNA and in particular of a modified Z-form provide a multitude of antigenic characteristics: the left-handed helicity, the zigzag dinucleotide phosphate repeat, the protruding purine substituents in the shallow major groove. It is not surprising then that the various antibodies obtained appear specific for different localized features of Z-DNA (33). The development of a specific chemical probe, so designed as to recognize a known structural element of Z-DNA, e.g. the helix handedness, would offer a simple complementary approach but has not heretofore been reported.

Enantiomeric selectivity has been observed in the interactions of tris(phenanthroline) metal complexes with B-DNA (15, 35-35). Experiments with tris(phenanthroline)zinc(II) have indicated stereoselectivity (15); dialysis of B-DNA against the racemic mixture leads to the optical enrichment in the Λ enantiomer. Subsequent luminescene, electrophoretic, and equilibrium dialysis studies of the well-characterized ruthenium(II) analogues have shown that the tris(phenanthroline) metal isomers bind to DNA by intercalation and it is the Δ enantiomer that binds preferentially to a right-handed duplex (34, 35). The enantiomeric selectively is based on steric interactions between the nonintercalated phenanthroline ligands and the phosphate backbone. Although the right-handed propeller-like isomer intercalates with facility into a right-handed helix, steric repulsions interfere with a similar intercalation of the Λ enantiomer.

Based on this premise, tris(phenanthroline) metal complexes appear useful in the design of probes to distinguish left-handed and right-handed DNA duplexes. The design flexibility inherent in metallointercalation reagents, in which both ligand and metal may be varied easily, makes the coordination complexes attractive probes (7, 8, 35). We have concentrated here on phenanthroline complexes of ruthenium(II) because of the high luminescence associated with their intense metal-to-ligand charge-transfer band (37, 38) and because the exchange-inert character of the low-spin $d^6$ complexes limits racemization (20).

Furthermore, there has been considerable interest in DNA endonucleolytic cleavage reactions that are activated by metal ions, (39, 40) both for the preparation of "footprinting" reagents (41) and as models for the reactivity of some antitumor antibiotics, notably bleomycin (42) and streptonigrin. (43) The features common to these complexes are that the molecule has a high affinity for double-stranded DNA and that the molecule binds a redox-active metal ion cofactor. The delivery of high concentrations of metal ion to the helix, in locally generating oxygen or hydroxide radicals, yields an efficient DNA cleavage reaction. Additionally, cobalt(III) bleomycin cleaves DNA in the presence of light. (44)

SUMMARY OF THE INVENTION

This invention concerns a coordination complex or salt thereof having the formula $(R)_3$—Co(III), wherein R comprises 1,10-phenanthroline or a substituted derivative thereof and R is bound to Co by a coordination bond.

One embodiment concerns a method for labeling DNA with a complex of the formula $(R)_3$—M, wherein R comprises 1,10-phenanthroline or a substituted derivative thereof, M comprises a suitable transition metal, and R is bonded to M by a coordination bond. In this and other embodiments a suitable transition metal is one which is capable of forming an octahedral complex with R, such as ruthenium (II) or cobalt (III). The invention also concerns a DNA molecule labeled with a complex of the formula $(R)_3$—M, as defined above, wherein the complex is bound to the DNA by intercalation.

Another embodiment of this invention is a method for selectively labeling Z-DNA with the lambda enantiomer of a complex of the formula $(R)_3$—M, as defined above. This method comprises contacting the lambda enantiomer of the complex under suitable conditions such that the complex binds to the Z-DNA. The invention further involves a labeled DNA molecule comprising Z-DNA and the lambda enantiomer of a complex of the formula $(R)_3$—M, as defined above, the complex being bound to the Z-DNA.

Another embodiment of this invention concerns a method for detecting the presence of Z-DNA. This method involves selectively labeling Z-DNA according to the above-mentioned method and detecting the presence of the complex bound to the Z-DNA.

Still another embodiment of this invention is a method for nicking double-stranded DNA by effecting breakage of at least one phosphodiester bond along the DNA. The method involves contacting the DNA with a cobalt (III)-containing complex of this invention under suitable conditions such that the complex intercalates into the DNA to form an adduct and irradiating the adduct so formed with a sufficient dose of ultraviolet radiation of an appropriate wavelength so as to nick the DNA at the site(s) of intercalation. This invention further involves a method for cleaving double-stranded DNA which comprises nicking the DNA by the above-mentioned method and treating the nicked DNA so produced with a suitable enzyme capable of cleaving single-stranded DNA under effective conditions to cleave the nicked DNA at the site of the nick(s).

An additional embodiment of this invention is a method for selectively nicking Z-DNA by effecting breakage of at least one phosphodiester bond along the Z-DNA. The method involves contacting a DNA molecule containing a Z-DNA sequence with a lambda enantiomer of a cobalt (III)-containing complex of this invention under suitable conditions such that the complex binds to the Z-DNA to form an adduct and irradiating the adduct so formed with a sufficient dose of ultraviolet radiation of an appropriate wavelength so as to nick the DNA at the binding site(s). Double-stranded Z-DNA may be selectively cleaved by selectively nicking the Z-DNA by the above-mentioned method and treating the nicked DNA so produced with a suitable enzyme capable of cleaving single-stranded DNA under effective conditions to cleave the nicked double-stranded DNA at the site of the nick(s).

This invention further concerns a method for killing a portion of a population of appropriate tumor cells. The method involves contacting the tumor cells under suitable conditions with an effective amount of the lambda enantiomer of a coordination complex of the formula $(R)^3$—M, as previously defined, to kill the tumor cells. In another embodiment a racemic cobalt-(III)-containing complex of the invention may similarly be used to kill tumor cells. When a cobalt (III)-containing complex is used, the method may further comprise irradiating the tumor cells with a suitable dose of ultraviolet radiation of an appropriate wavelength at a suitable time after the tumor cells have been contacted with the complex, permitting the complex to nick DNA.

Still another embodiment of this invention is a pharmaceutical composition for the treatment of tumor cells in a subject. The pharmaceutical composition comprises a pharmaceutically acceptable carrier and an effective anti-tumor amount of a cobalt(III)-containing complex of the invention or of the lambda enantiomer of a complex of the formula (R)$_3$—M, as defined previously. Such a composition may be used in a method for treating a subject afflicted with tumor cells so as to cause regression of the tumor cells. This method involves administering to the subject by a suitable route the pharmaceutical composition in an amount sufficient to cause regression of the tumor cells.

BRIEF DESCRIPTION OF THE FIGURES

FIG. 3. Relative mobilities of closed ($\bullet$) and nicked ($\circ$) circular pColE1 DNA in the presence of increasing concentrations of added $\Delta$- (above) and $\Lambda$- (below) (phen)$_3$Ru$^{2+}$. Bars indicate the width of the DNA bands on the basis of the distribution of topoisomers. Comigration points of nicked and closed circular DNAs are seen at 90 and 120 $\mu$M for the $\Delta$ and $\Lambda$ isomers, respectively.

Densitometric scans were performed on photographs using a Cary 219 spectrophotometer with gel scanning attachment. Band sizes were quantitated using markers of known molecular weight. Note that since the bands were stained with ethidium bromide, the band intensities are weighted by their molecular weight.

FIG. 13. Coarse map of left-handed sites in pBR322. (a) Densitometric scans of $\Lambda$-Co(DIP)$_3$$^{3+}$ fragmentation after linearization with EcoRI. Bands (in kilobase) are produced at 3.3 and 1.1, 2.75 and 1.45, and 2.2. Since EcoRI cleaves at position zero, these fragments correspond to recognition sites at 3.3, 1.45, and 2.2. (b) Biological map of pBR322 showing positions of cleavage by $\Lambda$-Co(DIP)$_3$$^{3+}$ ($\Lambda$).

FIG. 14. Schematic view of the enantiomers of (phen)$_3$Ru$^{2+}$ bound to B-DNA, illustrating the basis for stereo selectivity. Unfavorable steric interactions are seen between the nonintercalated ligands of the $\Delta$ isomer and the DNA phosphate backbone. In contrast the $\Delta$ isomer fits easily in a right-handed helical groove.

Figure 15A:
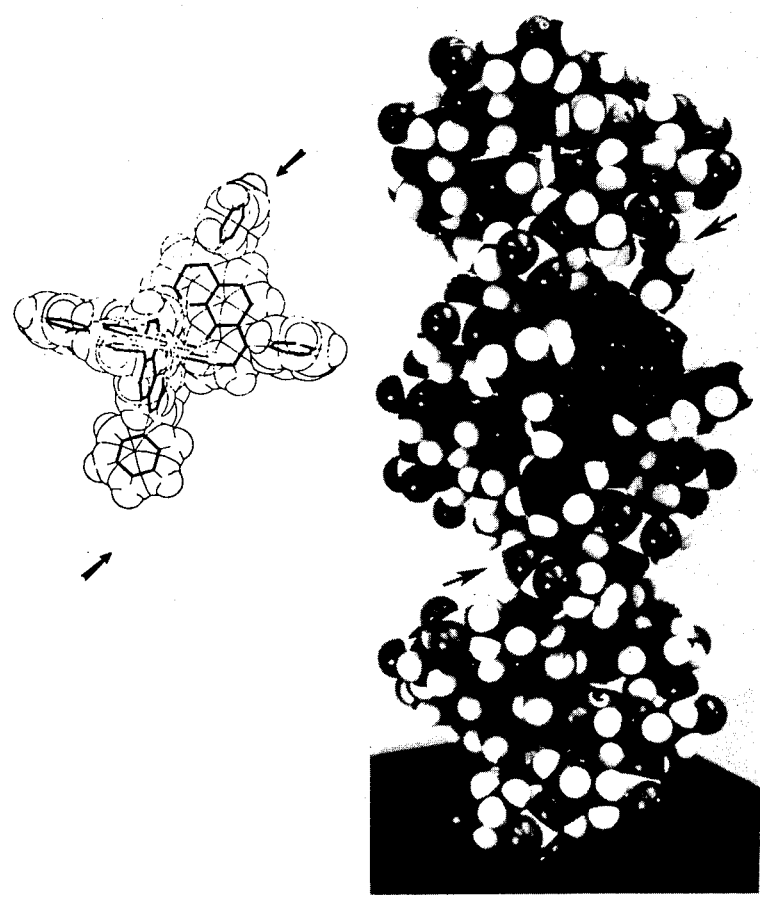
Figure 15B:
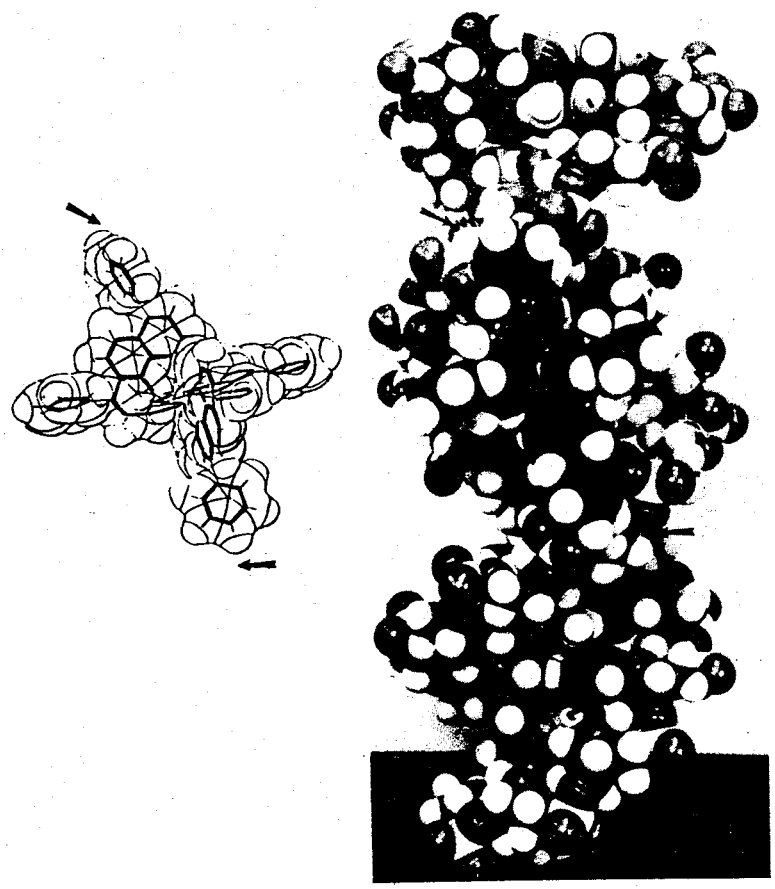

FIG. 15. Corey-Pauling-Kolton space-filling models of $\Delta$- and $\Lambda$-RuDIP with a right-handed B-DNA helix. The orientation of the metal complex in the helix is shown in the sketches. One ligand (not visible) is oriented perpendicular to the helix axis for intercalation between the base pairs. (A) Intercalation of the $\Delta$ enantiomer. The nonintercalated ligands fit easily within the right-handed groove. (B) For the $\Lambda$ enantiomer, when one ligand is positioned for intercalation, the remaining two ligands are blocked completely above and below (arrows) by the right-handed sugar-phosphate backbone, and this steric constraint prevents ligand insertion between the base pairs. This can also be seen by following the line of the DNA backbone, which, although completely visible in A, is interrupted by the phenyl groups of Λ-RuDIP in B.

DETAILED DESCRIPTION OF THE INVENTION

As mentioned above, this invention concerns a coordination complex or salt thereof having the formula $(R)_3$—Co(III), wherein R comprises 1,10-phenanthroline or a substituted derivative thereof and R is bound to Co by a coordination bond. A "substituted derivative" as the phrase is used herein is a compound obtained by replacing one or more hydrogen atoms present in 1,10-phenanthroline with one or more moieties having the characteristic that the complex containing the resulting compound binds to DNA. Merely by way of example, the substituted derivative of 1,10-phenanthroline may be 4,7-diamino-1,10-phenanthroline; 3,8-diamino-1,10-phenanthroline; 4,7-dimethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline, or 3,8-dispermine-1,10-phenanthroline. Unless otherwise specified the complex of this invention is a racemic mixture of enantiomers. The invention also concerns the optically resolved delta and lamda isomers of the complex.

One embodiment concerns a method for labeling DNA with a complex of the formula $(R)_3$—M, wherein R comprises 1,10-phenanthroline or a substituted derivative thereof as defined above, M comprises a suitable transition metal, and R is bonded to M by a coordination bond. In this and other embodiments a suitable transition metal is one which is capable of forming an octahedral complex with R, such a ruthenium (II) or cobalt (III). The labeling method involves contacting the DNA with the complex under suitable conditions such that the complex binds to the DNA, e.g. by intercalation.

The invention also concerns a DNA molecule labeled with a complex of the formula $(R)_3$—M, as defined above, and the complex is bound to the DNA, e.g by intercalation. Preferably the labeled DNA molecule is produced by the above-described method.

A further embodiment is a method for selectively labeling Z-DNA with the lambda enantiomer of a complex of the formula $(R)_3$—M, as defined above. This method comprises contacting the DNA with the lambda enantiomer of the complex under suitable conditions such that the complex binds to the Z-DNA. The invention further involves a labeled DNA molecule comprising Z-DNA and the lambda enantiomer of a complex of the formula $(R)_3$—M, as defined above, the complex being bound to the Z-DNA. Preferably the labeled DNA molecule is produced by the above-described method.

Another embodiment of this invention concerns a method for detecting the presence of Z-DNA. This method involves selectively labeling Z-DMA according to the above-mentioned method and detecting the presence of the complex bound to the Z-DNA, e.g. by spectroscopic methods (See Experiments hereinafter).

Still another embodiment of this invention is a method for nicking double-stranded DNA by effecting single-stranded scission, i.e., breakage of at least one phosphodiester bond along the DNA. The method involves contacting the DNA with a cobalt (III)-containing complex of this invention under suitable conditions such that the complex binds to the DNA, e.g. by intercalation, to form an adduct and irradiating the adduct so formed with a sufficient dose of ultraviolet radiation of an appropriate wavelength so as to nick the DNA at the site(s) of intercalation. An appropriate ultraviolet wavelength in this an other embodiments is a wavelength which is absorbed by the ligand bands of the complex used. As desribed hereinafter, the ligand band absorption of a complex of this invention may be determined spectroscopically by conventional methods.

This invention further involves a method for cleaving double-stranded DNA which comprises nicking the DNA by the above-mentioned method and treating the nicked DNA so produced with a suitable enzyme capable of cleaving single-stranded DNA under effective conditions to cleave the nicked double-stranded DNA at the site of the nick(s). By this method double-stranded scission of the DNA is effected. Suitable enzymes for effecting double-stranded cleavage of nicked DNA in this and other embodiments included those which are not deactivated in the presence of the complex used for DNA nicking, e.g. S1 nuclease.

An additional embodiment of this invention is a method for selectivity nicking Z-DNA by effecting breakage of at least one phosphodiester bond along the Z-DNA. The method involves contacting a DNA molecule containing a Z-DNA sequence with the lambda enantiomer of a cobalt (III)-containing complex of this invention under suitable conditions such that the complex binds to the Z-DNA to form an adduct and irradiating the adduct so formed with a sufficient dose of ultraviolet radiation of an appropriate wavelength, as previously defined, so as to nick the DNA at the binding site(s). Double-stranded Z-DNA may be selectively cleaved by selectively nicking the Z-DNA by the above-mentioned method and treating the nicked DNA so produced with a suitable enzyme capable of cleaving single-stranded DNA under effective conditions to cleave the nicked DNA at the site of the nick(s).

This invention further concerns a method for killing a portion of a population of appropriate tumor cells. The method involves contacting the tumor cells under suitable conditions with an effective amount of the lambda enantiomer of a coordination complex of the formula $(R)^3$—M, as previously defined, to kill the tumor cells. Alternatively, a racemic cobalt(III)-containing complex of this invention may be similarly used. When a cobalt (III)-containing complex is used, the method may further comprise irradiating the tumor cells with a suitable dose of ultraviolet radiation of an appropriate wavelength at a suitable time after the tumor cells have been contacted with the complex, permitting the complex to nick DNA.

Still another embodiment of this invention is a pharmaceutical composition for the treatment of tumor cells in a subject e.g. a human or animal. The pharmaceutical composition comprises an effective anti-tumor amount of the lambda enantiomer of a complex of the formula $(R)_3$—M, as defined previously, and a pharmaceutically acceptable carrier. Again, a racemic cobalt(III)-containing complex may be used alternatively. Preferably the complex is a cobalt(III)-containing complex. Suitable carriers include sterile saline or buffer-containing solutions or other carriers known in the art such as those used with cisplatin.

Such a composition may be used in a method for treating a subject, e.g. a human or animal, afflicted with tumor cells so as to cause regression of the tumor cells. This method involves administering to the subject by a suitable route the pharmaceutical composition in an amount sufficient to cause regression of the tumor cells. Suitable routes of administration include parenteral administration and topical administration, e.g. in cases such as skin cancers where the tumor cells are located on or near an exposed surface of the subject. Furthermore, if the complex used is a cobalt(III)-containing complex, the method may additionally involve irradiating the tumor cells with a suitable dose of ultraviolet radiation of an appropriate wavelength permitting the complex to nick DNA. In this method the irradiation should be conducted at a suitable time after administration of the compositon to the subject, i.e. to permit the complex to interact with the DNA. It should also be noted that optically resolved entantiomers of the complexes of this invention, specifically the lambda isomer, may provide superior results both in killing tumor cells and in treating subjects afflicted with tumor cells.

EXPERIMENTAL DETAILS

Octahedral complexes with three bidentate ligands like phenanthroline do not contain an inversion center, and therefore, as shown below, two enantiomeric forms are present. Note that the intercalating portion of the molecule, the phenanthroline ligand, is coordinated directly to the asymmetric center of the cation, the metal. Because this chiral metal center is really proximal to the site of intercalation, the interaction of these complexes with DNA provides a clear illustration of stereospecific drug binding to a similarly asymmetric DNA helix. Furthermore this stereospecific binding mode provides a means for designing probes for DNA helicity.

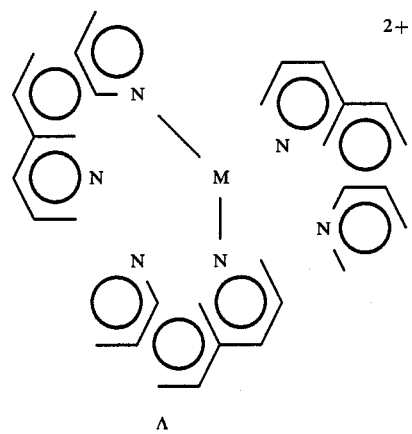

Λ

-continued

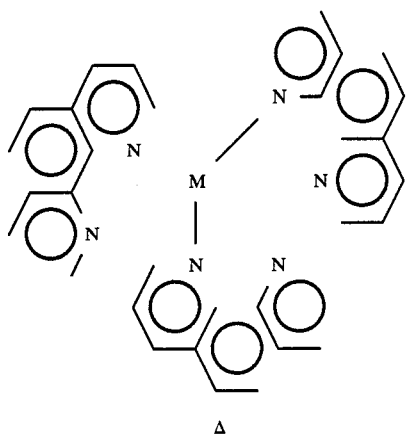

Δ

Ruthenium(II) complexes have been found useful because of (i) the kinetically inert character of the low-spin $d^6$ species, (ii) their intense metal to ligand charge-transfer (MLCT) band in the visible spectrum and since (iii) many chemical and spectroscopic properties of the poly(pyridine) complexes have been established. The electronic structure of the ground and excited states of tris(bipyridine)ruthenium(II) has been examined in detail. (45) The strong visible absorption band, distinct from the absorption of DNA, in $(phen)_3Ru^{2+}$ as well as its high luminescence provide spectroscopic tools to monitor the intercalative process. (38, 46) Most importantly, in contrast to $(phen)_3Zn^{2+}$, which is somewhat labile, (47) the ruthenium(II) complexes are essentially inert to racemization. (48)

Optical isomers of $(phen)_3Ru^{2+}$ may be isolated in pure form, (48, 49) and the absolute configurations have been assigned (50). Electric dichroism measurements of $(phen)_3Ru^{2+}$ bound to DNA have been conducted (51) and support the findings of enantiomeric selectivity.

Although a preference in binding is found between enantiomers in the phenanthroline series, both isomers do in fact intercalate into the right-handed helix as discussed above. To amplify the chiral discrimination and hence improves the sensitivity of the chiral probe, suitable substituents, e.g. amino-, ethylenediamino-, hydroxyl-, nitro-, phenyl- or spermine-substituents, may be added to each phenanthroline ligand at appropriate ring sites, e.g. 3,8- or 4,7. Bulky substituents at the distal sites on the cation can block completely the intercalation of the isomer into a right-handed helix, and thus provides selective spectroscopic probes for the handedness of the DNA duplex. The structure of the left-handed enantiomer of a preferred complex, Λ-tris(4,7-diphenyl-1,10-phenanthroline)ruthenium(II) (RuDIP), which binds to left-handed Z-DNA but not to right-handed B-DNA, is shown below.

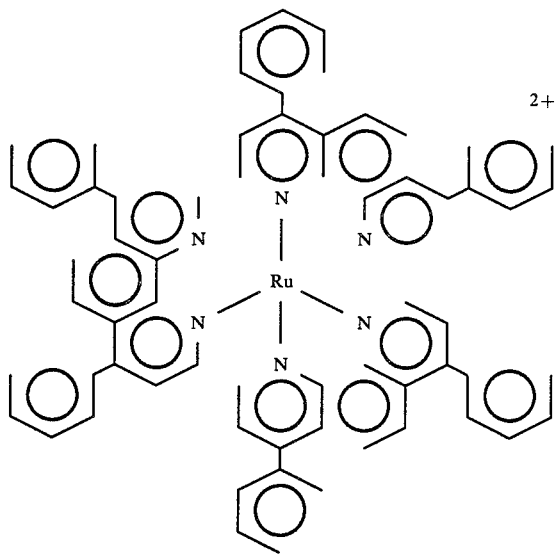

As for the smaller tris(phenanthroline) metal complexes, DNA binding is evident in the presence of racemic RuDIP. (52) The similarity to (phen)$_3$Ru$^{2+}$ in spectral characteristics on binding to DNA, i.e. hydrochromicty and luminescence enhancements, suggested that RuDIP also bonds to the duplex by intercalation. RuDIP is however substantially more bulky and hydrophobic than the parent (phen)$_3$Ru$^{2+}$ cation. Substitution of phenyl groups at the distal 4- and 7-positions leads to several significant perturbations. First, the solubility of the ruthenium complex in aqueous solution is diminished appreciably, which is a practical consideration. Second, stacking with the base pairs in the helix now requires that the phenyl groups rotate into the plane of the phenanthroline. The rotation to planarity can be accomplished with minimal steric interactions of the neighboring hydrogen atoms by lengthening the carbon-carbon bond between the phenyl and phenanthroline moieties; precedence for this type of structural distortion is found in the case of biphenyl which is planar when stacked in a solid state lattice. (53) The phenyl groups once rotated into the plane of the phenanthroline increase the surface area for base pair overlap substantially as compared with (phen)$_3$Ru$^{2+}$, stabilizing the intercalatively bound metal-DNA complex. An increased affinity for the helix is indeed apparent in gel electrophoresis experiments where changes in supercoiled DNA mobility are first evident at an order of magnitude lower total ruthenium concentration than for (phen)$_3$Ru$^{2+}$. Hydrophobic interactions of the non-intercalated ligands abutting the helical groove may also account for some increase in affinity for the duplex. Third, and perhaps most importantly, the added phenyl substituents increase the chiral discrimination markedly. While the delta isomer can still bind closely into the right-handed helix, intercalation of the lambda isomer is now completely blocked.

Figure 1:
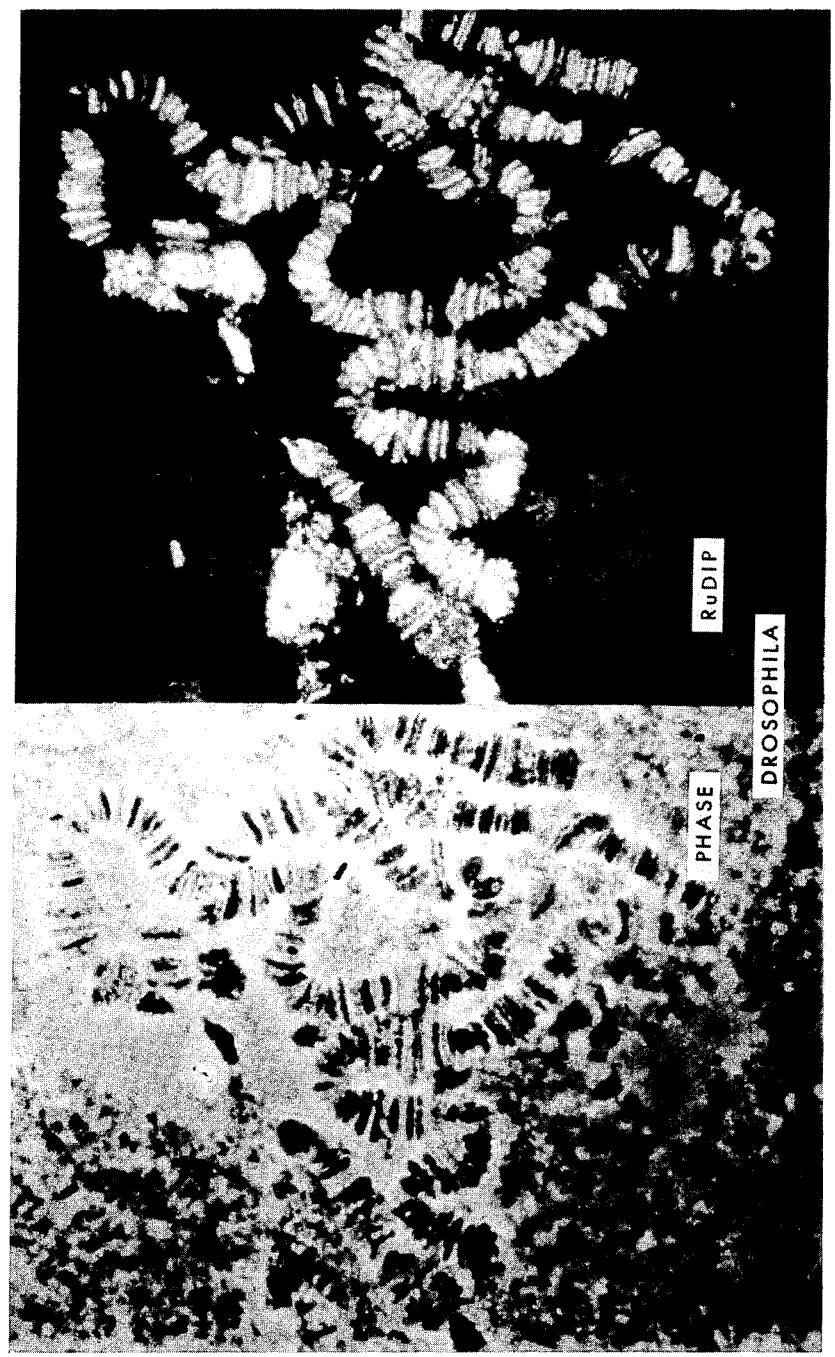
FIG. 1. Micrographs of Drosophila polytene chromosomes stained with racemic RuDIP by phase contrast (left) and fluorescent (right) microscopy. High concentrations of RuDIP, bright regions in the fluorescent micrographs, are found at the band regions (the dark regions by phase contrast).

Because the steric constraints are governed by the helicity of the duplex, RuDIP enantiomers can offer a specific chemical probe to distinguish right-handed and left-handed DNAs. While for the lambda isomer steric interactions between the non-intercalated phenyl groups and the DNA-phosphate backbone prevent close association to B-DNA, no similar repulsive interactions limit binding to the left-handed Z-DNA. (16) Hence an assay of duplex binding by the ruthenium enantiomers equivalently assays the DNA conformation. It is necessary at this point to note that RuDIP is indeed a probe for helical structure and does not itself promote a conformatioion transition between B- and Z-DNA. The circular dichroic spectra of poly(dGC) in the B-form or Z-form without ruthenium present are identical to those of DNA solutions containing ruthenium at an added ratio of 0.05 per nucleotide. Unlike other smaller intercalators which in binding at high drug/DNA ratios causes Z—B conformational transition (54, 55, 56), racemic RuDIP does not interconvert the helical forms. The enantiomers of RuDIP provide, therefore, a chemical means to examine DNA conformation and specifically, the handedness of the helix. DNAs of particular repetitive sequence or those covalently bound by particular drugs will be intriguing to study. Because of the high luminescence of the ruthenium complexes, some intersecting applications become feasible. FIG. 1 shows, for example, fluorescent micrographs (57) of Drosophila polytene chromosomes stained with racemic RuDIP. These samples were prepared in collaboration with Dr. O. J. Miller and Dr. D. Miller. Centers of high RuDIP concentration correlate closely with the band regions seen by phase contrast and no staining is evident in either interband regions or puffs. Experiments using the individual enantiomers can be conducted to determine whether a high local concentration of a particular conformation is present. These micrographs should provide a useful addition to those obtained through staining with fluorescent antibodies, (31) with the particular advantage of pointing out specific structural features depending upon the stereoselectivity observed.

Metallointercalation reagents also offer flexibility in the design of a stereospecific DNA nicking agent. Such agents have been prepared by using tris-phenanthroline complexes with a suitable choice of redox-active metal, e.g. cobalt. Tris(phenanthroline)cobalt(III) (58), for example, at low concentrations cleaves DNA when irradiated at 254 nm. Furthermore the high stereospecificity of the tris(diphenylphenanthroline) (DIP) metal isomers (59) with DNA helices is preserved in these cleavages reactions.

Numerous spectroscopic and x-ray crystallographic studies have shown that DNA may adopt a range of conformations, from the right-handed A- and B-forms to the striking left-handed Z-DNA helix (60, 61). Regions of conformational heterogeneity along the strand, such as cruciform structures, single-stranded loops, and left-handed segments, have been detected using DNA enzymes (62), and it has been suggested that local DNA conformation might play some role in regulating gene expression. Chiral metal complexes of this invention can intercalate into the helix and are therefore particularly advantageous in probing local DNA conformation (15, 34, 52, 64). Tris(diphenylphenanthroline) (DIP) ruthenium(II) complexes provide a spectroscopic probe for helix handedness; the lambda isomer, which does not bind B-DNA owing to steric constraints, binds avidly to Z-DNA (63). Upon photoactivation, the analogous cobalt isomers, Co(DIP)$_3{}^{3+}$, furthermore cleave DNA stereospecifically, providing a sensitive assay for local regions in the Z-form (64). The specific left-handed sites have now been mapped where Λ-Co(-DIP)$_3{}^{3+}$ cleaves in the plasmids pLP32 (29), containing a d(CG)$_{32}$ insert, and pBR322 (65). In pLP32 a primary cleavage occurs at the insert, and in native pBR322 cleavage occurs at four discrete sites: 1.45 kb, 2.3 kb, 3.3 kb, and 4.2 kb. These sites correspond to segments of alternating purine-pyrimidines. Moreover, these positions map to the ends of the three distinct coding regions in pBR322: the tetracycline resistance gene, the origin of replication, and either end of the ampicillin resistance (β-lactamase) gene. The locations of these left-handed segments suggest that Z-DNA might serve as a conformational punctuation mark to demarcate the ends of genes.

Λ-Co(DIP)$_3^{3+}$, the photoactivated DNA cleaving agent used here to detect Z-DNA segments is shown below.

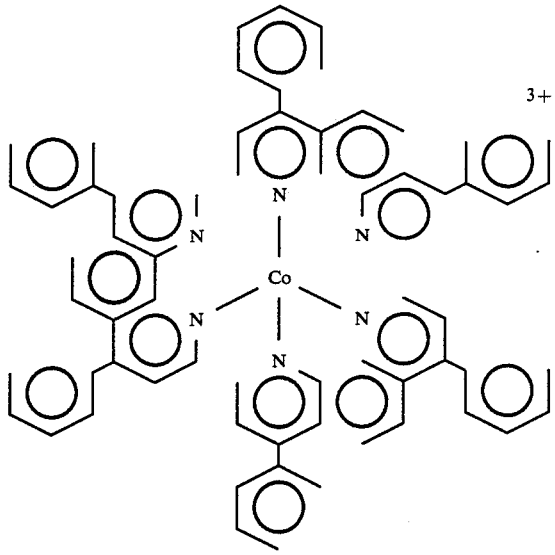

The possible application of the complexes of this invention in chemotherapy has also been investigated. Beyond the antimicrobial and antitumor activities common to intercalating agents, if Z-DNA is important in gene regulation, the stereospecific intercalators of this invention could display a unique potency in vivo. Preliminary experiments in tissue cultures have shown high toxicity without irradiation, and phototherapy may provide greater potency and tissue specificity.

EXPERIMENTS

Materials and Methods

I. Tris(phenanthroline)ruthenium II

Ruthenium Complexes

[(phen)$_3$Ru]Cl$_2$·2H$_2$O was prepared as follows: to a solution of 0.5 g K$_2$RuCl$_5$ in 50 ml hot water containing 1 drop 6N HCl was added 0.81 g phenanthroline monohydrate (Aldrich). The resulting mixture was boiled for 15 minutes to fully dissolve the ligand and thereafter 0.75 ml of 50% hypophosphorous acid neutralized with 2N NaOH was added. The solution was refluxed for 30 minutes and filtered hot to remove solid material. To the filtrate was added 10 ml 6N HCl, the volume reduced to about 20 ml and cooled at 0° overnight. Single orange crystals of [(phen)$_3$Ru]Cl$_2$ were obtained. See also (38). Enantiomers were obtained by successive diastereomeric recrystallizations with antimony D-tartrate anion. (49) At most, two recrystallizations were required to achieve [α]$_D$ 1317, after which point additional purification did not yield increased optical activity. Several samples of the Δ and Λ isomers were used in the course of the various binding studies, and, on the basis of comparison to literature values for the specific rotation, all showed a level of optical purity given by [(C(Δ-Ru)-C(Λ-Ru)/(C(Δ-Ru)+C(Λ-Ru))]≧0.92. The steroisomers were isolated as perchlorate salts; and elemental analyses (performed by Galbraith Lab., TN) were as follows: %C, 49.34; %H, 3.29; N, 9.52; calculated for [(phen)$_3$Ru](ClO$_4$)$_2$·2H$_2$O, %C, 49.32; %H, 3.22; %N, 9.59. Spectrophotometric and luminescence titrations of racemic Ru(phen)$_3$Cl$_2$ and equimolar mixtures of Δ- and Λ-Ru(phen)$_3$(ClO$_4$) with DNA agreed closely, indicating that the presence of perchlorate (≦50M) was without effect. Stock ruthenium solutions were either freshly prepared or kept in the dark. Concentrations of (phen)$_3$Ru$^{2+}$ were determined spectrophotometrically by using ε$_{447}$1900M$^{-1}$ cm$^1$. (38)

BUFFERS AND CHEMICALS

Experiments were carried out at pH 7.1 in buffer 1 (5 mM Tris, 50 nM NaCl), buffer 2 (5 mM Tris, 4.0M NaCl), or buffer 3 (50 mM Tris acetate, 20 mM sodium acetate, 18 mM NaCl pH 7.0). Solutions were prepared with distilled deionized water. Plasticware was used throughout and was cleaned by soaking overnight in 10% HNO$_3$ followed by exhaustive rinsing. Dialysis membranes were prepared by the following protocol: After they were boiled successively in sodium carbonate, 1% EDTA, and 1% SDS and exhaustively rinsed in deionized water, the membranes were heated to 80° C. in 0.3% sodium sulfite, acidified at 60° C. with 2% sulfuric acid, and thereafter rinsed again with deionized water and 1% EDTA. This procedure serves to minimize metal binding to the membranes.

Nucleic Acid

Calf thymus DNA, obtained from Sigma Chemical Co., was purified by phenol extraction as described previously. (9c) Poly(dGC)·poly(dGC) from P. L. Biochemicals Inc. and plasmid ColE1 from Sigma Chemical Co. were extensively dialyzed in buffer before use. DNA concentrations per nucleotide were determined spectrophotometrically by assuming ε$_{260}$ 6000M$^{-1}$ cm$^{-1}$ for calf thymus DNA and ε$_{260}$ 8400M$^{-1}$ cm$^{-1}$ for poly(dGC).

Spectroscopic Measurements

Absorption spectra were recorded on a Cary 219 spectrophotometer. Absorbance titrations of racemic, Δ- and Λ-(phen)$_3$Ru$^{2+}$ in buffer 1 were performed by using a fixed ruthenium concentration to which increments of the DNA stock solution were added. Ruthenium was also added to the DNA stock to keep the total dye concentration constant. Luminesence measurements were conducted on a Perkin-Elmer LS-5 flourescence spectrophotometer at ambient temperature. Samples were excited at 447 nm, and emission was observed between 500 and 700 nm. All experiments were carried out in buffer 1 with (phen)$_3$Ru$^{2+}$ concentrations typically of 10 μM and DNA phosphate/ruthenium ratios varying from 1 to 50. Lifetime measurements were performed on an Ortec 776 single-photon counter and timer in line with an Apple Computer. The samples were excited with a PRA 510A nanosecond lamp, and emission was observed at 593 nm. Reproducible lifetimes for the bound species in the presence of free ruthenium were obtained by neglecting the first 1.2 μs(2τ[Ru(phen)$_3^{2+}$$_{free}$]), of the decay curve.

Electrophoresis

Dye gel electrophoresis of supercoiled DNA in 1% agarose was performed in buffer 3 by using the method of Espejo and Lebowitz (6) modified as described previously.(15) Ruthenium concentrations in the gels were carefully determined on the basis of several absorbance readings of the stock concentrations for the enantiomers. Because of the high background luminescence of (phen)$_3$Ru$^{2+}$, gels were destained for 24 hours in buffer prior to staining with ethidium.

Equilibrium Dialysis

Binding isotherms were obtained on the basis of dialysis of calf thymus DNA in buffer 1 against (phen)$_3$Ru$^{2+}$ at 22° C. The DNA was dialyzed first exhaustively in buffer to remove small fragments. Thereafter, dialysis against ruthenium was allowed to continue for at least 24 hours after which time equilibration was achieved. Each sample consisted of 2 mL of dialysate containing Δ-, Λ-, or rac-(phen)$_3$Ru$^{2+}$, varying in concentration between 50 and 1,000 μM, and, within the dialysis bag, 1 mL of 1 mM DNA phosphate. To determine bound and free concentrations, absorbance spectra were taken of dilutions (3-50 μM). Free ruthenium concentrations outside the bag were determined on the basis of absorbance readings at 447 nm. For concentrations of ruthenium inside the bag, in the presence of DNA, readings were obtained at the isosbestic point, where ε$_{464}$ 13630 M$^{-1}$ cm$^{-1}$ (vide infra). Equilibrium dialysis of poly (dGC) was conducted similarly in buffer 2. Measurements of circular dichroism were obtained on a Jasco J-40 automatic recording spectropolarimeter. Because of the irregular baseline of the instrument, all spectra were digitized and replotted after base-line subtraction. Data analyses were performed on a IBM PC and a Digital VAX 11/780.

II. Tris(4,7-diphenyl-1,10-phenanthroline)rutheniumII

Nucleic Acids

Calf thymus DNA (Sigma) was purified by phenol extraction (66). Poly[d(G-C)] (P-L Biochemicals) was dialyzed at least three times before use. Experiments were conducted at pH 7.2 in buffer 1 [4.5 mM Tris.HCl/45 mM NaCl/150 μM Co(NH$_3$)$_6$Cl$_3$/10% dimethyl sulfoxide], buffer 2 [5 mM Tris.HCl/50 mM NaCl/150 μM Co(NH$_3$)$_6$Cl$_3$], or buffer 3 [5 mM Tris.HCl/4.0M NaCl]. DNA concentrations per nucleotide were determined spectrophotometrically assuming ε$_{260}$=6600 M$^{-1}$.cm$^{-1}$ for calf thymus DNA (67) and ε$_{260}$=8400 M$^{-1}$.cm$^{-1}$ for poly[d(G-C)] (68). In preparing Z-DNA, poly[d(G-C)] stock solutions were incubated in the cobalt hexammine buffer for 2-18 hr to ensure both a complete transition to the Z conformation and minimal aggregation. Stock solutions were examined spectrophotometrically and by CD before use.

Ruthenium Complexes

The synthesis of RuDIP trihydrate was carried out as described above, substituting 4,7-diphenyl-1,10-phenanthroline for the unsubstituted 1,10-phenanthroline. See also (38). Concentrations were determined spectrophotometrically using ε$_{460}$=2.95×10$^4$ M$^{-1}$.cm$^{-1}$. Elemental analyses were consistent with literature values. The Δ and Λ isomers were either separated by successive recrystallizations with the antimony tartrate anion in 50% ethanol or prepared by asymmetric synthesis in the presence of antimony tartrate and then recrystallized. Λ-RuDIP forms the less soluble diastereomeric salt with antimonyl D-tartrate. The separated isomers were isolated finally as perchlorate salts. The assignments of absolute configuration have been made on the basis of the relative binding affinities of these enantiomers for B-DNA (see below). Many rounds of recrystallization yielded a small quantity of Λ-RuDIP having [θ]$_{283}$=−4.0×10$^3$deg.M$^{-1}$.cm. This assignment is consistent with both the UV CD for tris(1,10-phenanthroline)ruthenium(II) [(phen)$_3$Ru$^{2+}$],assigned previously (31), and studies of the enantiomeric preference of (phen)$_3$Ru$^{2+}$ for B-DNA (34, 35, 51). The optical purities of the Δ- and Λ-RuDIP samples used below were 41% and 70%, respectively. Therefore the sample designated Δ-RuDIP contains 70.5% Δ isomer and 29.5% Λ isomer, and that designated Λ-RuDIP is composed of 14% Δ- and 86% Λ-RuDIP.

Spectroscopic Measurements

Absorbance spectra were recorded using a Varian Cary 219 UV/visible spectrophotometer and luminescence spectra, with a Perkin-Elmer LS-5 fluorescene spectrophotometer. Titrations were carried out using a constant ruthenium concentration (4-6 μM) to which increments of either calf thymus DNA or poly[d(G-C)] were added. Because RuDIP has limited solubility in aqueous solution (≦10 μM), dimethyl sulfoxide was included in buffer 1. CD spectra of B-DNA or Z-poly[d(G-C)] with 150 μM Co(NH$_3$)$_6$$^{3+}$ were unaffected by the presence of the dimethyl sulfoxide. Although more difficult, titrations in buffer 2 and buffer 3 were also conducted.

III. CobaltIII Complexes

Tris(4,7-diphenyl-1,10-phenanthroline)cobalt(III) (Co(DIP)$_3$$^{3+}$) tri-tartrate was prepared as follows: 4,7-diphenyl-1,10-phenanthroline (Aldrich) was dissolved in a minimum volume of ethanol to which one third stoichiometric CoCl$_2$.6H$_2$O was added. The green brown solution was oxidized by using Br$_2$/H$_2$0, and a heavy orange precipitate formed immediately. The solution was refluxed for 1 h, and concentrated hydrochloride was added. The bromine oxidation was then repeated. The crude chloride salt was used directly for enantiomeric separations. With either l- or d-tartaric acid (Aldrich), the deep red tartrate (Tar) diastereomeric salts [Λ-Co(DIP)$_3$].(L-Tar)$_3$ and [Δ-Co(DIP)$_3$.(d-Tar)$_3$, were prepared by successive recrystallizations in 50% ethanol, pH 7.0.

Chemical and spectroscopic data for these complexes are as follows: Anal. Calcd for [Co(DIP)$_3$](Tar)$_3$.H$_2$O(-CoC$_{84}$N$_6$O$_{19}$H$_{65}$) C, 66.32; H, 4.32; N, 5.52; Found: C, 65.87; H, 4.46; N, 5.78. Absorption spectra showed λ$_{max}$ at 278 and 312 nm (shoulder). The circular dichroic spectra resemble those of enantiomers of Ru(-DIP)$_3$$^{2+}$, and absolute configurations have been assigned on that basis.

IV. Cleavage Methods

[Co(DIP)$_3$](tartrate)$_3$ (10 μM) was added to pBR322 DNA (100 μM nucleotides) in 50 mM tris-acetate buffer containing 18 mM NaCl, ph 7.0. The 20 μl sample was then irradiated at 315 nm (with a 1000 W Hg/xenon lamp narrowed to 315.5 nm with a monochromometer) for 90 seconds and ethanol precipitated. The ethanol wash removes unreacted Co(DIP)$_3$$^{3+}$ as well as the metal and ligand products of the reaction. After resuspension in trisacetate buffer containing 50 mM NaCl and 10 mM MbCl$_2$, pH 7.0, restriction enzyme was added (either EcoRI, BamHI, AvaI of NdeI) using at least a threefold excess to insure complete linearization. This was incubated at 37° C. for 45 min. The pH of the reaction mixture was then lowered to 5.0 and 10 mM Zn(NO$_3$)$_2$ added along with 4 units of Sl nuclease, and the samples were incubated for 5 min. at 37° C. This step causes cleavage of the DNA by Sl opposite the site nicked by Co(DIP)$_3$$^{3+}$. Electrophoresis on 1% agarose gels followed (50 mM tris-acetate, 18 mM NaCl, pH 7.0) to resolve the double stranded fragments produced. In these experiments pBR322 sequences are numbered beginning at the EcoRI site according to Sutcliffe (65). Gels were stained with 5 μg/ml ethidium bromide for 0.5 hr then destained in buffer for 2 hr. Gels were photographed using a Polaroid 600 camera with a red filter and 615 positive/negative film and irradiated from below.

V. In vitro Screening

For cell culture studies, a modification of the techniques of Fischer (69) was used. The cells were incubated in McCoy's Medium 5A with 15% fetal calf serum. The initial inoculum was 40,000 to 60,000 leukemic cells/ml. For studies of the inhibition of cell growth, 0.1 ml of a 20-fold concentration of the drug in question was added to 2 ml of media containing $4 \times 10^4$ cells/ml in Linbro tissue culture multiwell plates and allowed to incubate at 37° C. in 5% CO$_2$ for 96 hr. By these times, growth to approximately 10$^6$ cells/ml occurred in the control wells. The contents of each well were agitated to resuspend the cells and counted on a Coulter Counter. The percentage of inhibition of growth and the concentrations inhibiting cell growth by 50% were calculated. Cell culture experiments were conducted with mouse leukemia cell lines L1210 and P815. The cell lines and growth medium may be obtained from the American Type Culture Collection (ATCC), Rockville, Md.

RESULTS

I. Tris(1,10-phenanthroline)ruthenium (II)

Spectroscopic Studies

Figure 2:
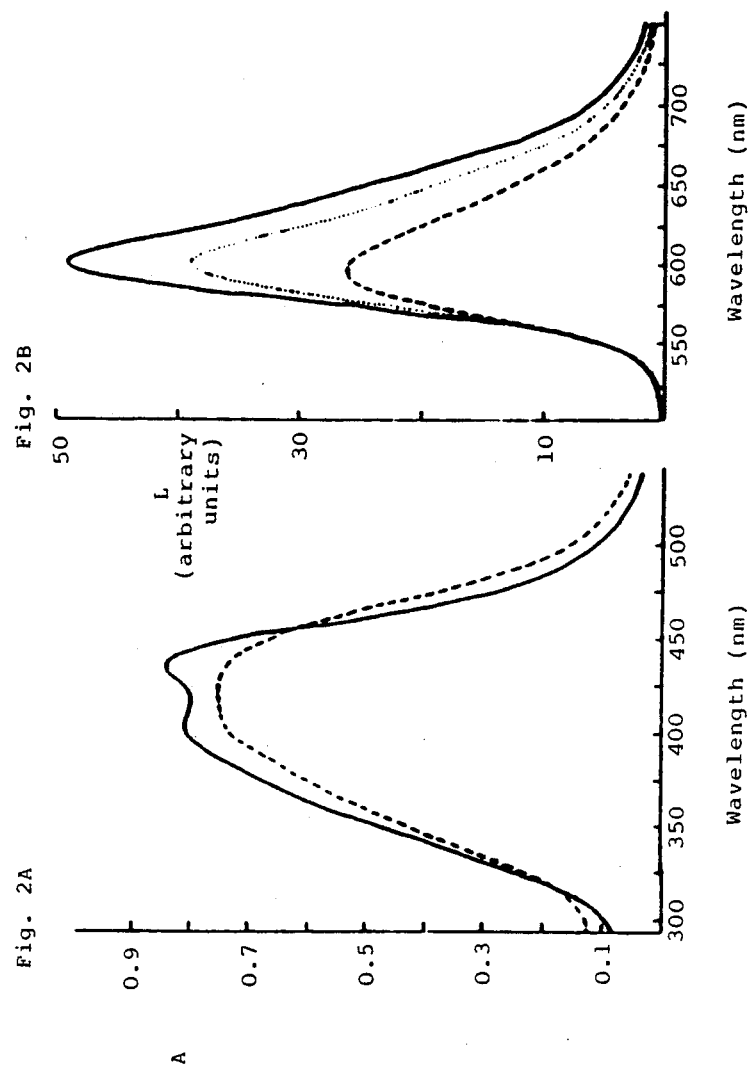
FIG. 2. (a) Visible absorption spectra of racemic (phen)$_3$Ru$^{2+}$ (50 $\mu$M) in the absence (—) and presence (- - -) of DNA (1 mM). (b) Luminescence spectra of free (- - -) (phen)$_3$Ru$^{2+}$ and of $\Lambda$-(phen)$_3$Ru$^{2+}$ (. . . ) and $\Delta$-(phen)$_3$Ru$^{2+}$ (—) in the presence of DNA (0.3 mM). Ruthenium concentrations were 10 $\mu$M. Sample excitation was at 447 nm.

The binding of Λ- and Δ-(phen)$_3$Ru$^{2+}$ to duplex DNA leads to a decrease and small shift in the visible absorption of the ruthenium species and a corresponding increase and shift in luminescence. FIG. 2 shows both the absorption spectra and luminescence spectra of (phen)$_3$Ru$^{2+}$ in the presence and absence of calf thymus DNA. The spectral changes observed here are often characteristic of intercalation.

The hypochromic shift in the broad charge-transfer band of (phen)$_3$Ru$^{2+}$ as a result of binding to the polynucleotide can be seen in FIG. 2A. A decrease of 12% in absorbance at 447 nm is found for the saturating DNA levels employed. Since at these concentrations 70% (phen)$_3$Ru$^{2+}$ is in the bound form, ε(bound)/ε(free)=0.83 at 447 nm. The hypochromic effect is small compared with that found for other intercalators, which may indicate that the charge is not being preferentially localized onto the intercalated ligand. Also for the free ruthenium complex the predominant polarization of the charge-transfer band is perpendicular to the molecular C3 axis (46) rather than parallel to the intercalative plane. Shown in the figure is the change in absorbance for the racemic mixture; also because the observable hypochromic effect is small, significant differences between enantiomers were not obtained. For both isomers a spectral shift of 2 nm to lower energy is found, which supports an electronic stacking interaction of the phenanthroline ligand with the base pairs of the helix. Isosbestic points at 355 and 464 nm are also apparent.

An enhancement in the luminescence of (phen)$_3$Ru$^{2+}$ on binding to duplex DNA parallels the observed hypochromicity. FIG. 2B shows the emission spectra of free (phen)$_3$Ru$^{2+}$ and of both lambda and delta isomers bound to DNA. These spectra also reveal a shift of 2 nm to longer wavelength with DNA binding. Moreover, in the presence of 0.25 mM DNA phosphate, emission increases of 48% and 87% are observed respectively for Λ- and Δ-(phen)$_3$Ru$^{2+}$ (10 μM). Note that a significant fraction of the ruthenium is free in the presence of the DNA at these concentrations, but the associated increase in solution viscosity for higher DNA concentrations precluded studies at saturating binding levels. The greater increase in luminescence seen for the Δ isomer in the presence of DNA over that for the Λ isomer indicates simply that a higher proportion of the Δ isomer is bound, rather than that their modes of association with the helix differ. Measurements of the excited-state lifetimes of enantiomers in the absence and presence of the DNA yielded results consistent with this interpretation. For Δ- and Λ-(phen)$_3$Ru$^{2+}$, determined separately and as a racemic mixture, identical experimental lifetimes of 2.0 and 0.6 μs were found respectively in the presence and absence of DNA. Both isomers therefore bind to the helix in a similar fashion, and indeed, if fully bound, would display similar enhancements in luminescence. Substantial increases in fluorescent lifetimes with intercalation have been observed in several instances (2-4, 70), notably for ethidium, and may be explained by the greater rigidity and lower collisional frequency of the molecule when stacked within the helix.

Measurements of Helical Unwinding

Both Λ- and Δ-(phen)$_3$Ru$^{2+}$ reversibly unwind and rewind supercoiled DNA as a function of increasing concentration of ruthenium(II), and for a given total concentration, a greater unwinding effect is evident for the Δ isomer. FIG. 3 illustrates the migration of pColE1 DNA through 1% agarose gels containing increasing levels of (phen)$_3$Ru$^{2+}$. Mobilities are plotted relative to the supercoiled DNA control to permit the inclusion of data from several gel electrophoresis trails. As can be seen in the figure, both isomers unwind the helix. With increasing levels of ruthenium bound, the duplex unwinds, and for a closed circle this unwinding results in first a release of negative supercoils at low levels bound and then the introduction of positive supercoils; the nicked DNA, without similar topological constraints, displays no variation in mobility. The bars in the figure indicate the width of the DNA bands, which vary because of the distribution of topoisomers in the sample. The observed duplex unwinding provides a strong indication of intercalative binding. Control experiments also show the unwinding to be reversible; preincubation of the DNA with ruthenium complex has no effect on gel mobility. It is interesting to note that no DNA cleavage is observed as a result of binding (phen)$_3$Ru$^{2+}$, even after irradiation with ultraviolet light (short wavelength) for 1 h.

For a given level of total ruthenium, a higher amount of duplex unwinding is found in the presence of Δ-(phen)$_3$Ru$^{2+}$, respectively. The comigration of nicked and closed circular DNAs occurs in the presence of 90 and 120 μM Δ-(phen)$_3$Ru$^{2+}$. This comigration point represents a fixed amount of helical unwinding. A lower added concentration of Δ-(phen)$_3$Ru$^{2+}$ is needed to unwind all the negative supercoils in the pColE1 DNA. These results therefore also reflect the higher affinity of the Δ isomer over the Λ isomer for the right-handed helix. At a given total concentration of ruthenium, more of the Δ isomer is bound and greater helical unwinding is evident. The alternative explanation for the lower concentration of the Δ isomer at the comigration point would be that the Δ isomer has a larger unwinding angle than the Λ isomer, so that the Δ isomer unwinds the duplex more per drug bound. A particularly large difference between unwinding angles (about 30%) would be needed to account for the electrophoresis results, however, and only small variations in unwinding angles are generally observed (4). Moreover larger, if any, structural perturbations should accompany binding of the Λ isomer to the right-handed helix rather than the Δ isomer. Here then, as well, the results show that the Δ isomer possesses a greater affinity for the DNA duplex.

These data may be used to estimate the intercalative unwinding angle. If we assume for the racemic mixture that the average comigration point of nicked and closed forms occurs with 100 μM ruthenium, then, on the basis of our determination of the binding constant provide (in-fra), a binding ratio of 0.089 per nucleotide is required to unwind fully the supercoils in the plasmid. Interestingly this value is identical with that calculated for ethidium, since in buffer 3 the comigration of nicked and closed pColE1 species in the presence of $5 \times 10^{-7}$M dye was observed. Therefore the unwinding angle for (phen)$_3$Ru$^{2+}$ is estimated to be the same as that for ethidium (6).

Equilibrium Dialysis Experiments

Figure 4:
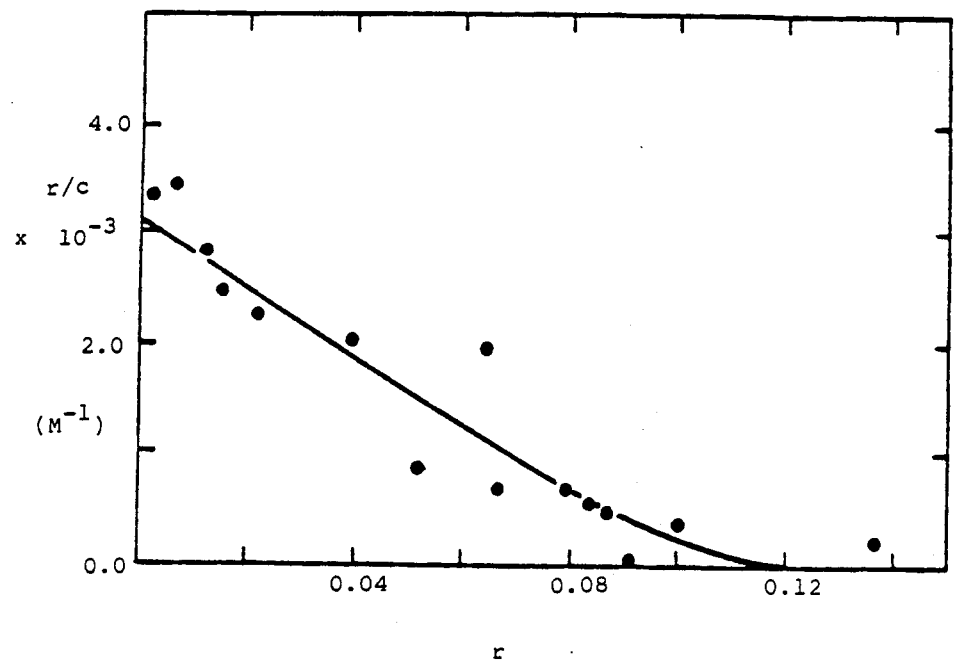
FIG. 4. Scatchard plot of (phen)$_3$Ru$^{2+}$ binding to calf thymus DNA in buffer 1 at 22° C., where r is the ratio of bound ruthenium to nucleotide concentrations and C is the concentration of ruthenium free in solution. The solid curve represents the best fit to eq 1.

The results of dialysis of calf thymus DNA with racemic (phen)$_3$Ru$^{2+}$ at 22° C. in buffer 1 are shown in FIG. 4 in the form of Scatchard plat (71). The data have been fit by nonlinear least-squares analysis to the following equation governing noncooperative binding to the helix, as derived by McGhee and von Hippel (72):

$$\frac{r}{C_F} = \frac{K(O)}{2} (1 - 2Lr) \left( \frac{1 - 2Lr}{1 - 2(L-1)r} \right)^{L-1} \quad (1)$$

where r is the ratio of the bound concentration of ruthenium to the concentration of DNA phospate, $C_F$ is the concentration of ruthenium free in solution, K(O) is the intrinsic binding constant, and the integer I, which measures the degree of anticooperativity, is the size of a binding site in base pairs. In fitting the data, the binding parameter K(O) was varied for several integer values of L. The best fit, shown as the solid curve in FIG. 4, yielded a binding constant K(O)=$6.2 \times 10^3$M$^{-1}$ (±2%) and an exclusion site size (L) of four base pairs. Data from luminescence titrations were consistent with this curve. The binding constant is quite low in comparison to values of $3 \times 10^5$ and $5 \times 10^4$M$^{-1}$ (extrapolated to the ionic strength of our buffer) for ethidium and [(phen)Pt(en)]$^{2+}$, respectively (73). The lower affinity of (phen)$_3$Ru$^{2+}$ is not surprising since only partial stacking of the phenanthroline ligand is feasible in this octahedral complex; greater overlap of the phenanthroline with the base pairs may be achieved in the square-planar platinum(II) species. The steric bulk of the nonintercalated ligands determines also the large four base-pair site size compared to a two base-pair (neighbor excluded) site for basically planar reagents (9, 74). Inspection of space-filling models show that the perpendicular phenanthroline ligands each span two base pairs either above or below the intercalatively bound phenanthroline, which is consistent with the binding isotherm.

Figure 5:
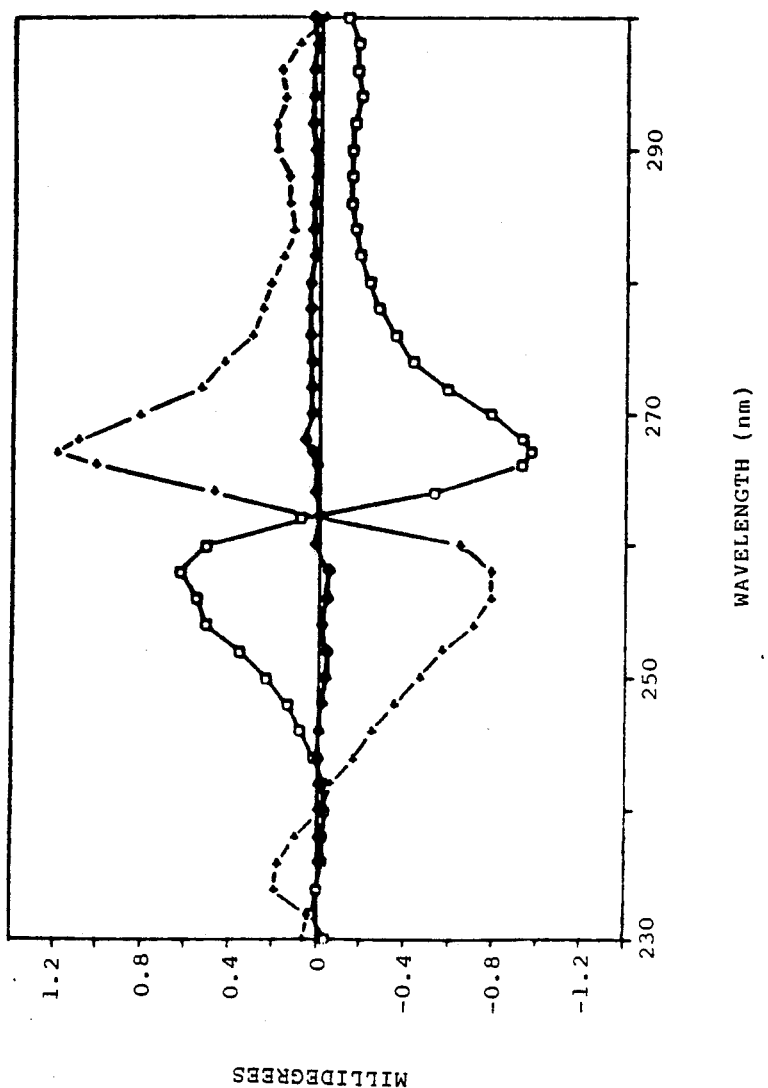
FIG. 5. Circular dichroism of ($\square$) $\Delta$-(phen)$_3$Ru$^{2+}$ and of solutions after dialysis of rac-(phen)$_3$Ru$^{2+}$ against (+) B-DNA and ($\blacksquare$) Z-DNA. Dialysis against B-DNA leads to enrichment of the solution in the unbound $\Lambda$ isomer.

In these equilibrium dialysis experiments of the racemic mixture, the relative binding of the two enantiomers to the polynucleotide may be determined sensitively on the basis of the degree of optical enrichment on the unbound enantiomer in the dialysate. FIG. 5 shows the circular dichroism ($1.5 \times 10^{-5}$M) of the dialysate after equilibration of calf thymus DNA (1 mM) with racemic (phen)$_3$Ru$^{2+}$ ($2 \times 10^{-4}$M). Also shown for comparison is the circular dichroism of Δ-(phen)$_3$Ru$^{2+}$ (0.2 μM). The spectra show clearly that the dialysate has been optically enriched in the less favored isomer. The Δ enantiomer binds preferentially to the right-handed helix. The degree of chiral discrimination may be made more quantitative by comparing the level of optical enrichment (2% for the sample shown) with the overall amount of ruthenium bound. On the basis of a simple competition between the enantiomers for sites along the helix with no cooperativity and, for simplification, describing the binding by each enantiomer in terms of the familiar Scatchard equation, X, the ratio of binding constants K(Δ)/K(Λ) may be calculated as follows:

$$X = (PK(\Delta)(n - r) + 1) \frac{(C_B + \Delta C)}{(C_B - \Delta C)} - PK(\Delta)(n - r) \quad (a)$$

where P is the concentration of DNA phosphate, n is the ratio of drug to DNA phosphate bound at saturation, taken as 0.125, $C_B$ is the total concentration of ruthenium bound, and ΔC is the difference in free concentrations between Δ and Λ isomers as measured by the intensity in the circular dichroism. Measurements of several samples yielded values of 1.1–1.3 for X. Thus the binding affinity of Δ-(phen)$_3$Ru$^{2+}$ is found to be 10–30% greater than Λ-(phen)$_3$Ru$^{2+}$ for calf thymus DNA by this method. This value is comparable to the differences seen in luminescence and unwinding experiments. Since the overall binding of (phen)$_3$Ru$^{2+}$ is small, binding isotherms obtained through equilibrium dialysis tended to show some scatter. A direct comparison of the binding isotherms for the enantiomers in equilibrium dialysis experiments using the pure isomers therefore could not be achieved; significant differences were not evident. Interestingly it appears that the method of optial enrichment yields the most sensitive assay for the differential binding.

Since the enrichment experiment provides the most sensitive method to examine enantiometric discrimination, poly(dGC) in 4M NaCl was also dialyzed against rac(phen)$_3$Ru$^{2+}$ to test for any enantiomeric preferences in binding to a left-handed DNA helix (16, 17). At the low binding levels examined, the circular dichroism of the polymer remains inverted, indicating that racemic (phen)$_3$Ru$^{2+}$ did not induce a Z-- B transition. After equilibrium dialysis with bound concentrations comparable to those in earlier experiments using calf thymus DNA, e.g., under conditions where low levels of enrichment could be detected, no optical activity was observed in the dialysate. Therefore, although intercalative binding had occurred, given similar spectral characteristics as in binding to the right-handed helix, no preference in binding was evident. In FIG. 5 the essentially base line spectrum of a solution after dialysis against Z-form poly(dGC) has also been included. This lack of discrimination for (phen)$_3$Ru$^{2+}$ is understandable in view of the shallow, almost grooveless character of the left-handed Z-DNA helix.

II. Tris(4,7-diphenyl-1,10-phenanthroline)ruthenium(II)

Figure 6:
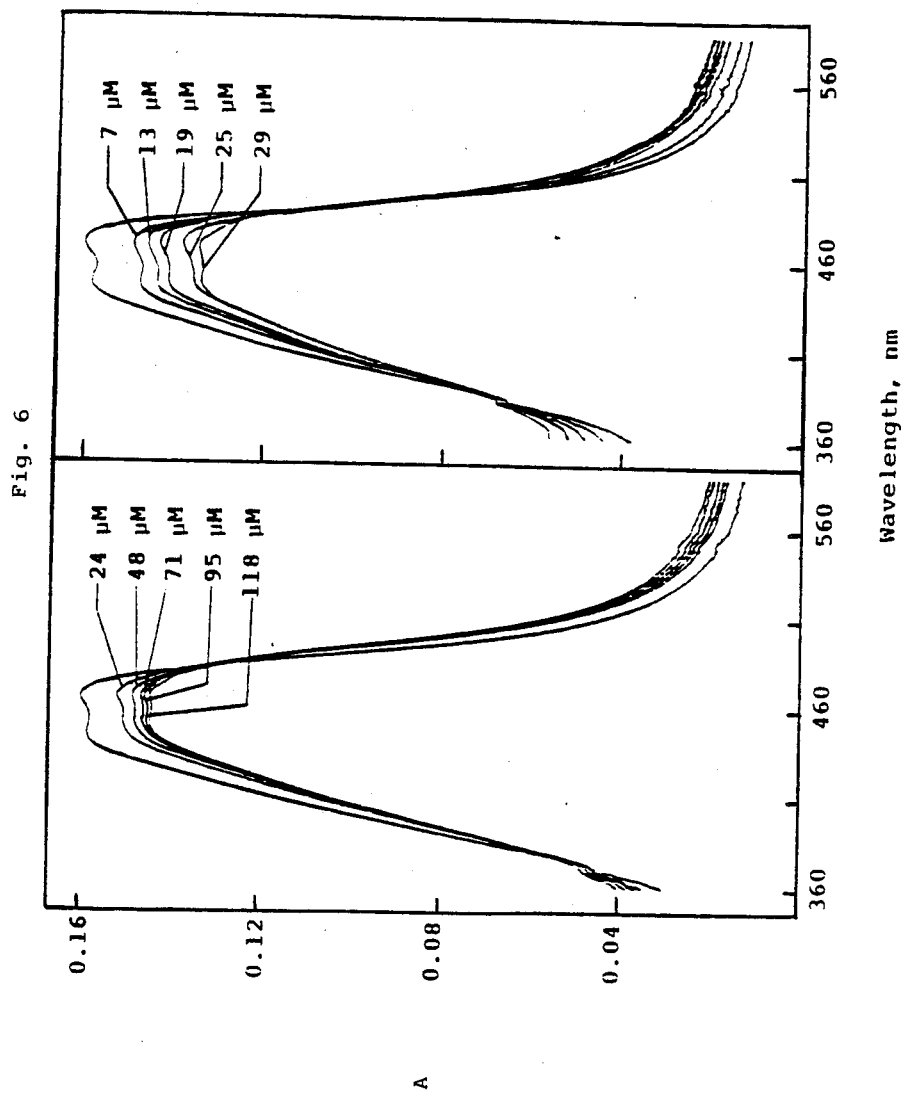
FIG. 6. Visible absorption spectra of racemic RuDIP (5.3 $\mu$M) in the absence and presence of various concentrations of B-form calf thymus DNA (Left) and Z-form poly[d(G-C)] (Right) in buffer 1.

In spectroscopic studies of racemic RuDIP with B- and Z-DNA, changes are seen in both the visible absorption and luminescence spectra of RuDIP on addition of either B- or Z-form DNA. Hence, binding may be monitored sensitively using either spectroscopic technique. Visible absorption titrations of racemic RuDIP in buffer 1 (described below) with calf thymus DNA and Z-form poly[d(G-C)] are shown in FIG. 6. The overall similarity of these titrations is apparent. Binding of either duplex DNA leads to hypochromicity in the intense metal-to-ligand charge-transfer band of the ruthenium complex. A small red shift (about 2 nm) in the spectrum of the bound complex and an isosbestic point at 485 nm can be seen. That spectral changes occur as a function of addition of either DNA form suggests that racemic RuDIP binds to both B- and Z-DNA. The similarity in spectral changes most likely reflects a similar mode of association of the ruthenium complex with either the right-handed B-DNA helix or the left-handed Z-DNA helix.

Differences in binding to the two forms are evident, however. A greater reduction in the absorption intensity of Ru-DIP accompanies binding to Z-form poly[d(G-C)] than to the B-DNA helix. In FIG. 6, for example, the apparent reduction in intensity with the addition of a 13:1 ration of calf thymus DNA-phosphate/ruthenium is only 9% whereas, for the left-handed helix, the reduction occurring at a nucleotide/ruthenium ratio of 5:1 is 17%. The greater hypchromicity in binding to Z-DNA is explained in part by the different stereoselectivities governing binding to each helix. Although both enantiomers bind to Z-DNA, only the Δenantiomer may bind easily to right-handed B-DNA. The differences in stereoselectivity cannot fully account for the difference in hypochromicity, however, because the hypochromicity in spectra of racemic RuDIP with Z-DNA is more than twice that observed with calf thymus DNA. If one assumes that the extinction coefficients for RuDIP when bound to each helix are the same, which seems reasonable based on the equal isosbestic points observed, then the larger hypochromic effect with Z-DNA suggests that both RuDIP enantiomers possess a greater affinity for Z-form poly[d-(G-C)] than for calf thymus DNA. Equilibrium dialysis experiments support this conclusion.

Figure 7:
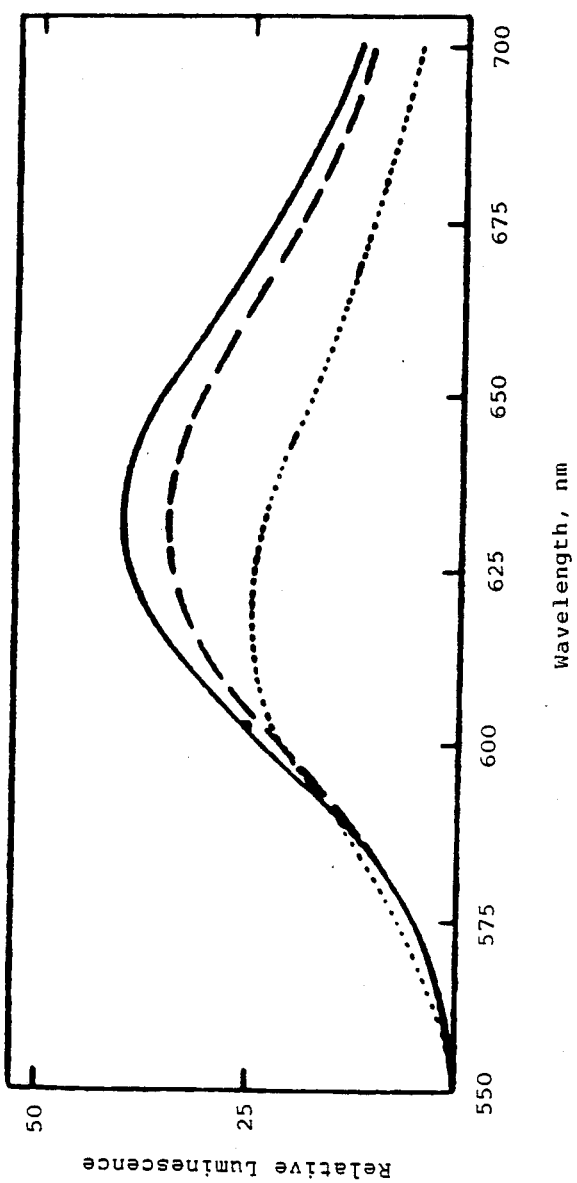
FIG. 7. Luminescence spectra in buffer 2. . . . , Racemic RuDIP (3 $\mu$M) free in solution; - - -, racemic RuRIP (3 $\mu$M) in the presence of Z-form poly[(G-C)]; —, B-form half calf thymus DNA. Samples were excited at 482 nm.

The luminescence of RuDIP is also enhanced on binding to the DNA duplex. FIG. 7 shows the emission spectrum of racemic RuDIP (3 μM) in the absence and presence of calf thymus DNA and Z-form poly[d(G-C)] (15 μM nucleotide). The shift in the spectrum to lower energy is particularly pronounced despite the broad nature of the transition; the maximum shifts 10 nm to longer wavelength in the presence of DNA. Greater luminescence is seen here on binding to B-DNA, despite the lower apparent affinity for this helix. In buffer 2, at a DNA-phosphate/ruthenium ratio of 5:1, the emission intensity of racemic RuDIP increases by 30% and 47% in the presence of Z-form poly[d(G-C)] and calf thymus DNA, respectively. The different enhancements may depend in part on nucleic acid composition as well as duplex conformation, RuDIP bound to B-form poly[d(G-C)] yields less luminescence than when bound to calf thymus DNA, despite having an equal affinity for these polynucleotides.

Racemic RuDIP appears to bind to both B- and Z-DNA rather than promoting a transition from one conformation to the other. CD spectra of Z-form poly[d(G-C)] in Co(NH$_3$)$^{3+}$ (buffer 1) or in 4M NaCl (buffer 3) are unaltered by the addition of racemic RuDIP at a nucleotide/ruthenium ratio of 10. Conversion of the Z-form to B-form with RuDIP is inconsistent also with the differential hypochromism and luminescence observed. If RuDIP promoted a Z to B transition, albeit inefficiently, rather than binding to both B- and Z-helices, then both the reduction in absorbance and the enhancement in luminescence observed on addition of Z-DNA would be less than or equal to that found with B-DNA, i.e., in proportion to the fraction of DNA converted. Instead significantly greater hypochromism is found when Z-DNA rather than B-DNA is added to the racemic mixture or indeed to each enantiomer individually. Therefore racemic RuDIP must bind to both DNA conformations. Consistent with these results, a conformational transition from Z-DNA to B-DNA would not be expected if the affinity of the metal cation for the Z-form were greater than that for the B-form. The ethidium cation, which binds to B-DNA by intercalation, is known to promote a Z to B transition at high binding ratios (75, 76) and presumably possesses a greater affinity for the B-form helix. The substantially larger RuDIP cation cannot saturate the DNA to comparable levels, which may be an important distinction. Moreover, although the ethidium ion can fully intercalate into B-DNA, RuDIP cannot and the nonintercalating ligands of RuDIP may dominate its interactions with the duplex.

Figure 8:
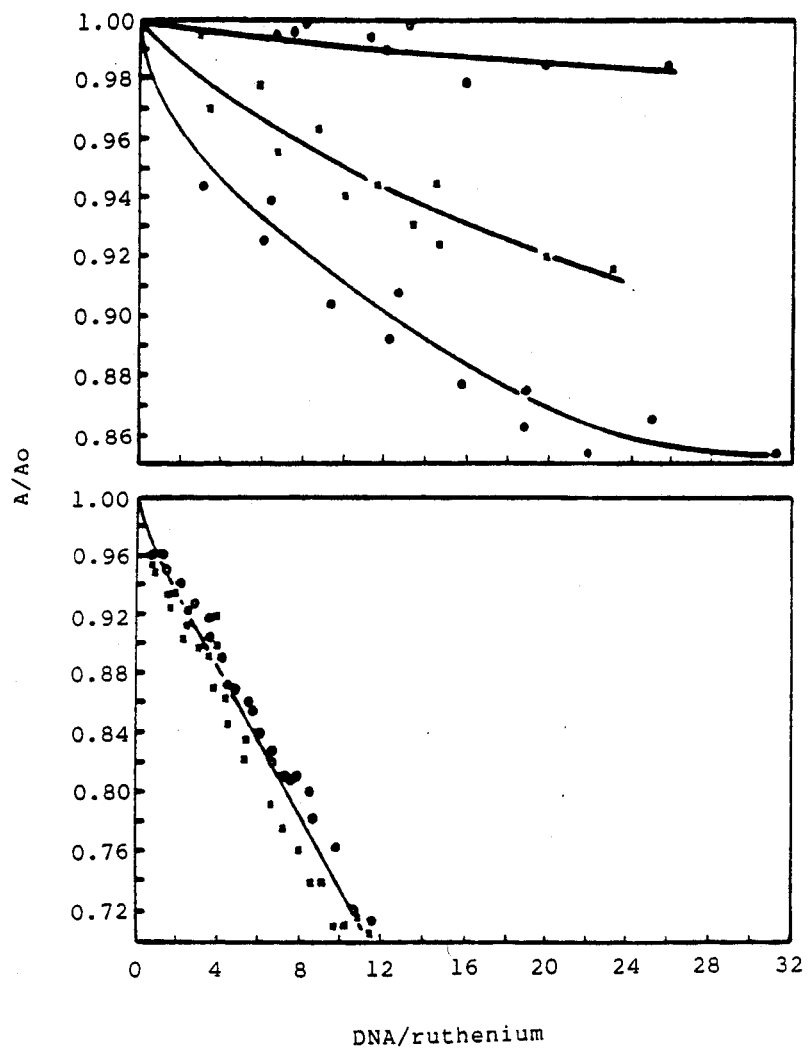
FIG. 8. Relative change in absorption intensity at 460 nm of racemic RuDIP (x), $\Lambda$-RuDIP ($\circ$), and $\Delta$-RuDIP ($\bullet$) at various DNA-phosphate/ruthenium ratios. Titrations were conducted in buffer 1 using either B-form calf thymus DNA (Upper) or Z-form poly[d(G-C)] (Lower). Strong stereoselectively with B-DNA is evident based on the differential hypochromism seen between enantiomers, whereas comparable titrations with Z-DNA show the same hypochromic effects with each enantiomer. Because large hypochromicity in the $\Lambda$ isomer is seen only with Z-DNA, $\Lambda$-RuDIP provides a probe for this conformation.

The utility of the RuDIP enantiomers as a probe for helical conformation becomes apparent when the binding characteristics of each enantiomer to B- and Z-DNAs are compared. Plots of the relative absorbance at 460 nm of the individual enantiomers as a function of the addition of either B-form calf thymus DNA or Z-form poly[d(G-C)] in buffer 1 are shown in FIG. 8. Based on the presence or absence of hypochromicity, it is clear that although RuDIP binds to B-DNA, the Λ isomer does not. Δ RuDIP does however bind to Z-DNA. Indeed, with Z-DNA no stereospecificity is observed. Hence the assay of duplex binding by the Λ isomer yields a sensitive assay for the Z-DNA conformation.

Strong enantiomeric selectivity governs the interaction of RuDIP with the right-handed D-DNA helix. The decrease in absorbance with increasing DNA concentration observed for the Λ, racemic mixture, and Δ samples can be fully accounted for based on the percentage of the Δ enantiomer present in the particular preparation (see Experimental). The pure Λ enantiomer does not bind to B-DNA. The presence of the phenyl groups at the 4 and 7 positions of the nonintercalated phenanthroline ligand has served to amplify the chiral discrimination. In comparison, differences in binding of (phen)$_3$Ru$^{2+}$ enantiomers had been seen only in spectrophotometric titrations at high DNA/ruthenium levels; the ratio of the affinities for B-DNA of $\Delta$ to $\Lambda$ isomers is about 1.3(34, 35). For RuDIP, with hydrogen atoms now replaced by phenyl groups, instead of simple interference with the DNA phosphate oxygen atoms, one finds that the steric bulk of the phenyl groups completely blocks interactions of the isomer in the right-handed gove. $\Delta$-RuDIP, however, binds with facility to a right-handed helix, indeed more avidly than $\Delta$-(phen)$_3$Ru$^{2+}$. This striking amplification in enantiomeric selectivity for RuDIP compared with (phen)$_3$Ru$^{2+}$ strongly supports our model for stereospecific intercalation.

Z-DNA serves as a poor template to discriminate between the enantiomers; identical reductions in absorbance intensity are found for the $\Delta$ and $\Lambda$ isomers (FIG. 8). Because of the shallow and very wide character of the major groove in Z-DNA, there are no steric constraints comparable with that found with B-DNA. Hence, if the binding modes are equivalent, no chiral specificity would be expected. The similarity in spectral characteristics of RuDIP in binding to the different DNA duplexes points to this similarity in binding modes. However, the lack of chiral specificity in binding to Z-DNA does limit what can be said at present about the interaction of RuDIP enantiomers with a Z-form helix. Based on relative hypochromicities, it appears that both $\Lambda$ and $\Delta$-RuDIP possess greater affinities for Z-form poly[d(G-C)] than for B-DNA. Hydrophobic interactions with the helical surface may lend some stability to the bound complex(77). The difference in affinity furthermore does not reflect a preference for base composition. Titrations of racemic RuDIP with B-form poly[d(G-C)] in buffer 1 lacking cobalt hexammine showed hypochromicity equal to that seen with calf thymus DNA. Also, cobalt hexammine itself does not appear to alter binding to the helix. RuDIP titrations using calf thymus DNA with and without Co(NH$_3$)$_6$$^{3+}$ were identical. In addition, the interaction cannot be explained purely be electrostatic interactions. Although smaller, hypochromic effects, approximately one-third of that shown here, are found in titrations in 4M NaCl (buffer 3) with either poly[d(G-C)] or calf thymus DNA. Partial intercalation into the DNA by both RuDIP enantiomers would be consistent with these results. It is finally important to note that the similar titrations of both enantiomers that are seen with Z-DNA but not with B-DNA suggest that neither enantiomer converts the Z-form helix to the B-DNA conformation. If that were the case, selectivity between the enantiomers would become apparent.

III. Cobalt(III) Complexes

Figure 9A:
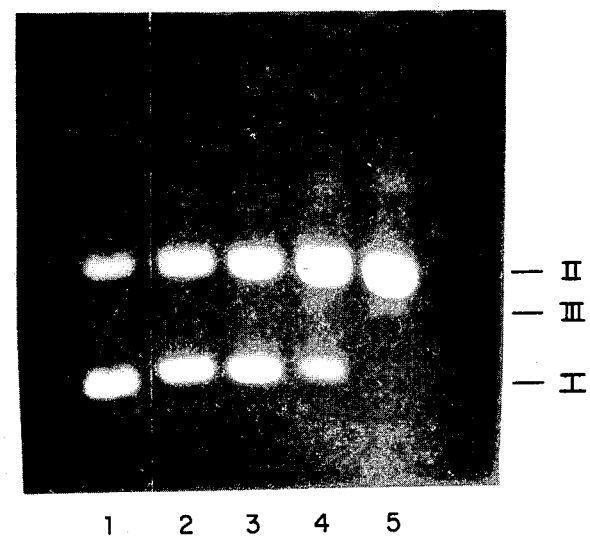
FIG. 9. (A) Cleavage of plasmid ColE1 DNA in the presence of (phen)$_3$Co$^{3+}$ and light. The 1% agarose gel shows the distribution of DNA forms (100 $\mu$M nucleotide) initially without cobalt (lane 1) and after irradiation at 254 nm (4-W mercury lamp) in the presence of 10 $\mu$M Co(phen)$_3$$^{3+}$ for 0, 20, 40, and 60 min (lanes 2–5, left to right). The samples were incubated in 50 mM Tris acetate buffer, pH 7.0, and 18 mM NaCl and then electrophoresed for 1 h at 60 V and stained with ethidium. (B) The cleavage is also stereoselective. Plasmid ColE1 DNA (100 $\mu$M) was incubated with $\Lambda$- (left) or $\Delta$-Co(-DIP)$_3$$^{3+}$ (right) (5$\mu$M) and irradiated for 0, 0.5, 1.0, or 1.5 h (lanes 1–4 and 5–8 for the $\Lambda$ and $\Delta$ isomers, respectively). Incubation of this DNA with $\Lambda$-Co(DIP)$_3$$^{3+}$ in light has no effect, while incubation with $\Delta$-Co(-DIP)$_3$$^{3+}$ in light causes complete conversion of form I to form II.

FIG. 9 shows gel electrophoretic separations of plasmid ColE1 DNA after incubation with cobalt complexes and irradiation for variable times. DNA cleavage is followed by monitoring the conversion of supercoiled (form I) closed circular plasmid DNA to the nicked circular form (form II) and linear (form III) species. (The original ColE1 pareparation contained 60% form I and 40% form II molecules). FIG. 9A reveals the complete conversion of form I to II after a 1-h irradiation in the presence of 10 $\mu$M (phen)$_3$CO$^{3+}$. Neither irradiation of the DNA at these low intensities without cobalt nor incubation with cobalt without light yielded significant strand scission. (Irradiation at 310 nm where there are strong ligand transitions also leads to cleavage). It is likely that the reduction of Co(III) is the important step leading to DNA cleavage and not that irradiation provides a means to generate cobalt(II) in situ. DNA incubation with the tris(phenanthroline) complex initially in the cobaltous form yielded no reaction unless irradiated. Presumably the cobaltous complex is oxidized in solution to the cobaltic species, since it is the +3 oxidation state in cobalt polyamine complexes that is photochemically active. Also dithiothreitol inhibits activity of Co(phen)$_3$$^{3+}$, perhaps by precluding regeneration of an active cobalt(III) species. This finding is in contrast to the iron and copper systems whose thiols are thought to stimulate activity by generating the metal species in the reduced form (39–43). Interestingly, electrophoresis also reveals with increasing irradiation a small reproducible increase in the mobility of form II; this may reflect some short-range radical-induced DNA cross-linking (78).

The cleavage reaction is furthermore strongly stereospecific. FIG. 1B shows pColE1 DNA of low superhelical density after incubation with either $\Lambda$-Co(DIP)$_3$$^{3+}$ or $\Delta$-Co(DIP)$_3$$^{3+}$ (17, 18) and irradiation with ultraviolet light. Incubation of pColE1 DNA of low superhelical density with the $\Lambda$ isomer, which cannot bind to a right-handed duplex owing to steric constraints, yields no appreciable reaction (19), whereas incubation with $\Delta$-Co(DIP)$_3$$^{3+}$, which is able to associate closely with right-handed B-DNA, shows efficient nicking activity comparable to that seen with Co(phen)$_3$$^{3+}$. Nicking was observed, however, upon titration of pColE1 of increasing superhelical density with $\Lambda$Co(DIP)$_3$$^{2+}$. This different cleavage efficiency by each enantiomer is consistent with the earlier finding (7) of conformational discrimination by the ruthenium(II) isomers; one enantiomer of Ru(DIP)$_3$$^{2+}$ binds to B-DNA, but both $\Delta$- and $\Lambda$-Ru(DIP)$_3$$^{2+}$ binds to the left-handed Z-DNA helix. These results underscore the importance of an intimate association of the metal with the duplex.

In FIG. 9B the overall concentrations of the cobalt isomers are equal, yet the $\Lambda$ trication, if it cannot intercalate, does not yield DNA strand scission.

Figure 10:
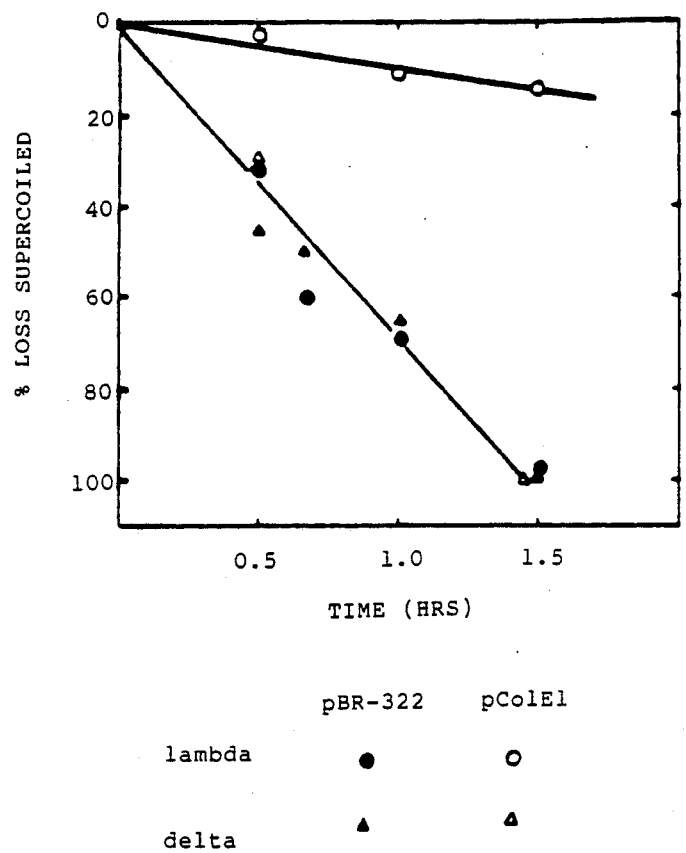
FIG. 10. Plot showing the percent reduction in form I band intensity for pBR322 DNA (closed symbols) and pColE1 DNA (open symbols) incubated with either $\Delta$-(triangles) of $\Lambda$-Co(DIP)$_3$$^{3+}$ (circles) (5 82 M) as a function of time irradiated. Extensive strand scission is evident in pBR322 with both isomers.

The $\Lambda$-tris(phenanthroline) metal complexes do, however, bind to left-handed Z-DNA (21, 22). We examined the plasmid pBR322 containing a 42-base pair alternating guanine-cytosine insert (pLP42) (29, 79) and which was shown (28, 17) to adopt the Z-conformation in 4M NaCl. Under these conditions, cleavage by both Co(DIP)$_3$$^{3+}$ enantiomers is obtained. Hence the isomer may recognize and cleave left-handed helices. More interesting, however, is the finding, plotted in FIG. 10 as percent loss of supercoiled form, that the plasmid pBR322 at physiological salt concentrations and without extreme superhelix underwinding also is significantly cleaved by the isomer. Given our other results of differential binding based on DNA helicity (35, 63) and the differential cleavage of ColE1 of low superhelical density described above, it appears that $\Lambda$-Co(DIP)$_3$$^{3+}$ might bind to and cleave a natural left-handed segment in pBR322 DNA of low superhelical density in normal salt concentrations. These observations support the findings by Rich and co-workers (80) of anti-Z antibody binding to the 14-base pair alternating purine-pyrimidine segment in pBR322). The statistically significant 14 base pair sequence (CACGGGTGCGCATG) in pBR322 shows alternation of purine and pyrimidine with one base out of register. Alternating purine-pyrimidine sequences tend to adopt the Z conformation. The plasmid pColE1 sequence contains no comparable stretch of alternation.

IV. Cleavage Site Mapping

Figure 11:
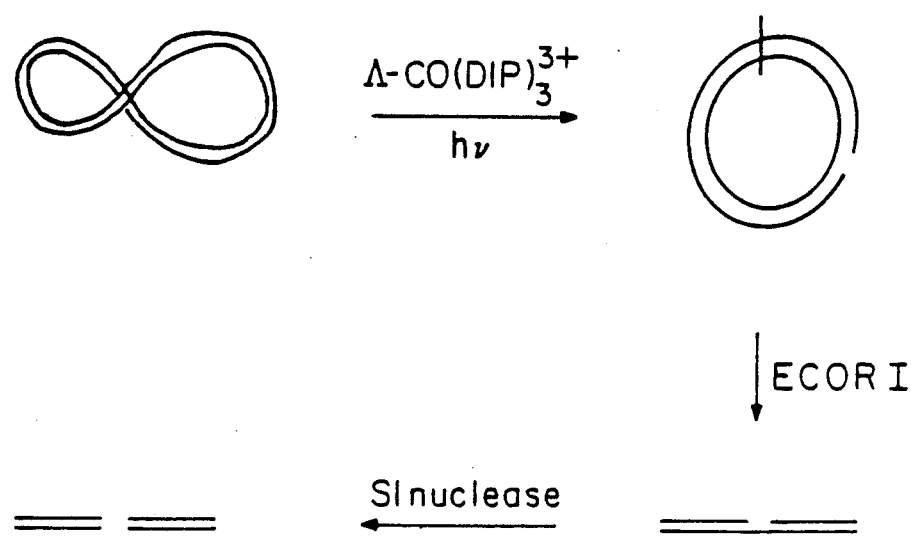
FIG. 11. Experimental scheme used to map the single-stranded cleavage sites of Co(DIP)$_3$$^{3+}$.

Irradiation at 315 nm of $\Lambda$-Co(DIP)$_3^{3+}$ (10 μM) solutions containing supercoiled pLP32 or pBR322 yields nicked circular form II DNAs. Photoreduction of Co(DIP)$_3^{3+}$ enantiomers bound to DNA leads to oxidative single-strand scission at the DNA binding site (64). In order to establish that cleavage and therefore binding occurs at discrete sites, the scheme outlined in FIG. 11 was employed. Following irradiation of Co(DIP)$_3^{3+}$-DNA samples and the production of nicked circles, the DNAs were linearized using a restriction enzyme which is known to cleave the plasmid at only one site along the strand. Subsequent treatment with S1 nuclease, which is specific for single-stranded regions, cleaves the DNA only opposite to the cobalt-induced nick producing a pair of linear fragments. From the sizes of these fragments, determined based upon their gel electrophoretic mobilities relative to markers, the distance of the cleavage site from the restriction site origin may be obtained. In order to distinguish whether the site is clockwise or counterclockwise to the origin, at least two restriction enzymes which cut at sufficiently distinct locations were examined. It is important to notice that this procedure yields distinct fragments only if binding and subsequent cleavage occurs at discrete sites. Non-specific cleavage produces fragments of all sizes and hence a smear on the gel; thus the presence of some contaminating form II DNA just alters the background intensity. Control experiments of sample irradiated without cobalt or cobalt binding but without irradiation yielded no distinct bands. Non-specific DNA damage as a result of irradiation was negligible. Controls showed that full linearization of the plasmid was essential, however, to avoid mapping S1 hypersensitive sites (62). Some restriction enzymes did not yield complete linear digests, either because of thymine dimer formation at the restriction site or inhibition due to Co(DIP)$_3^{3+}$ reaction, and these were not used. Finally, samples were irradiated only for short times so that no more than one nick per plasmid would occur. The fact that the sizes of pairs of fragments must sum to 4363 base pairs provided a useful experimental redundancy. By this general procedure the coarse map of $\Lambda$-Co(DIP)$_3^{3+}$ cleavage sites in any plasmid may be obtained.

Figure 12:
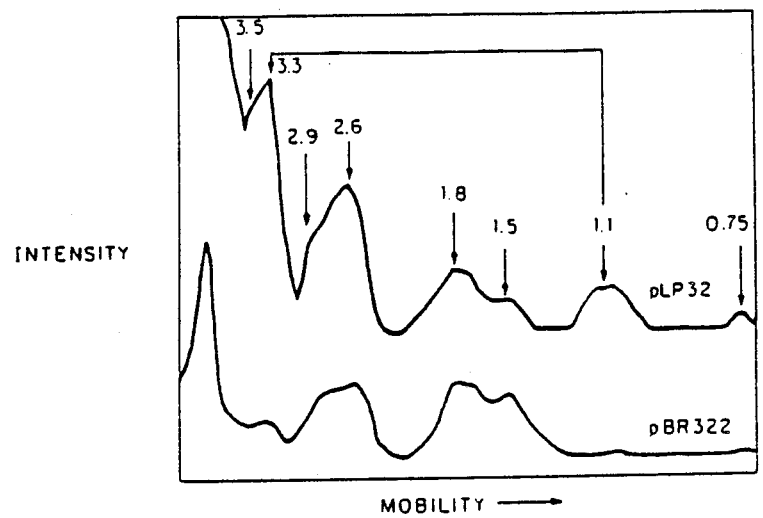
FIG. 12. Densitometric scans of $\Lambda$-Co(DIP) fragmentation using the scheme depicted in FIG. 1. The double stranded fragments produced in pBR322 using AvaI for linearization are the following sizes in kilobase pairs (kb): 3.5 and 0.75, 2.9 and 1.5, 1.8. Note that these pairs of bands sum to 4.4 kb, the length of the plasmid. In pLP32, a pair of bands not present in pBR322 are seen at 3.3 and 1.1 kb. These bands indicate cleavage at the d(CG)$_{32}$ insert at position 375 (1.1 or 3.3 from the AvaI site at 1424). This plasmid was a gift of Dr. A. Nordheim.

The plasmid pLP32 which contains a Z-DNA segment at a well-defined location (29, 81) was examined first. The plasmid had been constructed by inserting a d(CG)$_{32}$ fragment into the filled-in BamHI site (position 375) of pBR322 (29). The densitometric scan of the AvaI digest after reaction with $\Lambda$-Co(DIP)$_3^{3+}$ is shown in FIG. 12. In addition to the linear form several bands and shoulders are evident; their sizes in kilobase pairs (kb) are indicated in the figure. The appearance of the pair of fragments at 3.3 kg and 1.1 kg from the AvaI site (position 1424) shows that a major cleavage point is indeed at the Z site. Parallel digestion with NdeI established this position uniquely. More interesting perhaps is the comparison to the AvaI digest of pBR322, the same plasmid but lacking the insert. The pattern here is identical except that it lacks the 3.3 kb and 1.1 kb fragments. In pLP32, then, the cobalt complex must recognize and cleave a site not present in pBR322, the Z-form d(CG)$_{32}$ insert. The result demonstrates that the complex can cleave specifically at a left-handed site.

Other conformations are not similarly accessible to the chiral cobalt complex. $\Lambda$-tris(diphenylphenanthroline) complexes or ruthenium(II) and cobalt(III) do not react as assayed spectrophotometrically (34, 63) (for ruthenium) and by cleavage assays (64) (for cobalt) with B-form helices. The delta isomer in contrast can bind both B- and Z-forms and photolysis experiments using $\Delta$-Co(DIP)$_3^{3+}$ show non-specific cleavage of the linear DNA but with some specific band formation. It has also been found that (phen)$_3$Ru$^{2+}$ complexes do not bind significantly to double-stranded RNA and hence it is unlikely that $\Lambda$-Co(DIP)$_3^{3+}$ would recognize an A-form helical conformation. Additionally, racemic Co(DIP)$_3^{3+}$ cleavage of single-stranded phage DNA X174 was examined. Here after photolysis about 12% cleavage was observed, less than the 15% double-stranded content in the X174 sample, calculated based upon hypochromicity. It is unlikely then that Co(DIP)$_3^{3+}$ enantiomers could recognize open looped regions of a plasmid. Instead the only DNA conformation for which appreciable binding and cleavage by $\Lambda$-Co(DIP)$_3^{3+}$ has been found is Z-DNA.

Figure 13A:
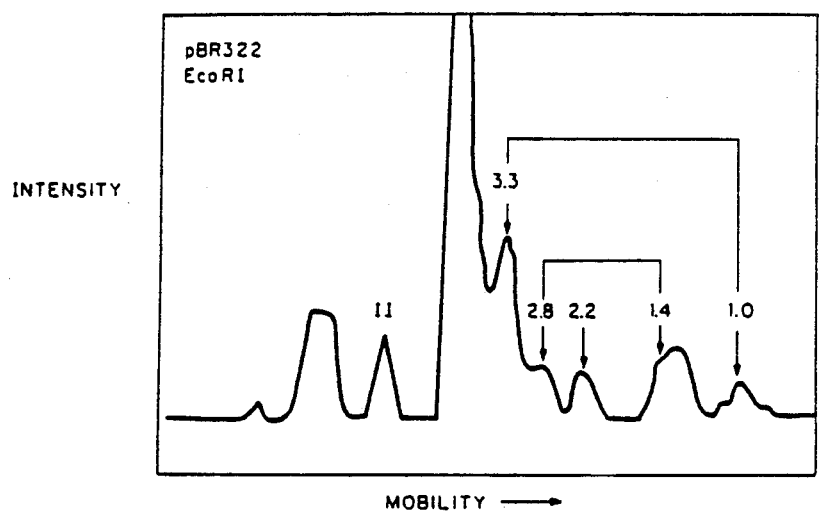

Photolysis and digestion of both pLP32 and pBR322 actually yields several distinct fragments, seen in FIG. 12, and therefore additional cleavage sites for $\Lambda$-Co(DIP)$_3^{3+}$, similar structurally to the lefthanded d(CG)$_{32}$ insert must be present in these plasmids. Based upon numerous trials using either EcoRI, BamHI, AvaI, or NdeI for linearization, there appears to be four discrete cleavage sites in pBR322, given in order of intensity 1.45±0.05 kb, 3.3±0.1 kb>4.24±0.02 kb>2.25±0.07 kb. The standard deviations are based upon averaging at least seven experiments. The plasmid pLP32 shows cleavage at these same positions in addition to cleavage at the insert. FIG. 13A shows a typical EcoRI digest. Fragment pairs are evident and, since EcoRI linearizes at the origin, the lengths of one fragment of the pair shows the position in kilobases of the site. The relative intensities, weighted by the fragment molecular weight, reflects either the relative site affinity for $\Lambda$-Co(DIP)$_3^{3+}$ or relative cleavage efficiency at a site. Variations in relative site intensities as a function of irradiation time and also as a function of salt concentration in the incubation mixture was observed. The influence of salt and superhelical density on the relative expression of these sites is currently being examined. The weakest site recognized is consistently at 2.3 kb. Table 1 summarizes the specific sites in pBR322 found with cleavage by $\Lambda$-Co(DIP)$_3^{3+}$.

TABLE 1

| $\Lambda$-Co(DIP)$_3^{3+}$ Cleavage Sites | |
|---|---|
| | Alternating Purine-Pyrimidine Sequences |
| 1.45 ± 0.05 kb | 1447-1460 |
| | CACGGGTGCGCATG |
| 2.25 ± 0.07 kb | 2315-2328 |
| | CGCACAGATGCGTA |
| 3.32 ± 0.11 kb | 3265-3277 |
| | GTATATATGAGTA |
| 4.24 ± 0.02 kb | 4254-64 |
| | TCCGCGCACAT |

V. In vitro Screening

Diphenyl tris complexes of this inventions were screened for cytotoxic activity against mouse leukemia cells as previously described. The results of two of the complexes are set forth in Table 2.

TABLE 2

Cytotoxicity of Cobalt and Ruthenium Complexes

| Compound | Cell Line[1] | ID$_{50}$ (μg)/ml |
|---|---|---|
| Ru(DIP)$_3$Cl$_2$ | L 1210 | 4.49 |
|  | P 815 | 5.42 |
| Co(DIP)$_3$.(d-tartrate)$_3$ | L 1210 | 0.51 |
|  | P 815 | 0.52 |

[1]L 1210 and P 815 are mouse leukemia cell lines, see Burchenal, J. H. et al., CANCER RESEARCH, 42:2598-6000 (July 1982)

DISCUSSION

I. Tris(phenanthroline)ruthenium(II)

Results of experiments described above indicate that tris(phenanthroline)ruthenium(II) binds to DNA by intercalation. The optical changes on binding to DNA agree with those seen for other intercalators. Hypochromicity in the metal to ligand charge-transfer (MLCT) band is observed and represents an overall 17% decrease in intensity. Stacking interactions with the base pairs lead to hypochromic shifts in the II→II* transitions of organic intercalating dyes, and it is interesting that the II symmetry of the MLCT preserves the hypochromic effect. Substantial increases in the luminescence of (phen)$_3$Ru$^{2+}$ also accompany binding to the duplex. The enhancement in emmission and corresponding increased luminescent lifetimes may simply reflect the decreased mobility of the complex when sandwiched into the helix. Emission lifetimes are comparable to those found for (phen)$_3$Ru$^{2+}$ in sodium lauryl sulfate micelles.(82) In addition to perturbations in the electronic structure of the bound reagent, intercalation leads to hydrodynamic changes in the DNA duplex. With increasing concentrations, (phen)$_3$Ru$^{2+}$ reversibly unwinds and rewinds superhelical DNA. Although not absolutely definitive,(4) this result provides a very strong indication of intercalation. Surely helical unwinding and lengthening accompany the binding of (phen)$_3$Ru$^{2+}$. Finally the binding isotherms obtained by equlibrium dialysis yield parameters that are reasonable for the intercalative mode of association. The complex binds to duplex DNA with relatively low affinity and, when bound, encompasses a four base-pair site. The octahedral coordination around the metal precludes effective stacking of the complex between base pairs. if the complex is viewed with one of the three phenanthroline ligands inserted into the helix, then the other two ligands actually protrude above and below the face of this phenanthroline and decrease the effective area of overlap. Hence only partial insertion is possible, which accounts for the low binding constant. The fact that so small a region of overlap with only partial insertion is necessary for a stabilizing interaction with the duplex is interesting to consider with respect to the binding of aromatic amino acid residues to DNA. The four base-pair site size is similarly consistent with the structural model for the bound complex, presented herein, where one ligand intercalates and the remaining two ligands span the groove of the helix. A site size of four base pairs is understandable since the internuclear distance of 10.4 A between distal hydrogen atoms on the ligands not only exceeds the 10.2 A of a single interbase pair site but must result in partial blockage of the next neighboring base pair both above and below the plane of insertion.

Furthermore the direct comparison between enantiomers of spectroscopic features, binding properties, and structural parameters establishes that the Δ enantiomer possesses the greater affinity for a right-handed helix. Intercalation of tris(phenanthroline)ruthenium(II) into the duplex imposes different steric constraints on Δ and Λ isomers, and it is this difference that determines the enantiomeric selectivity. Perhaps the strongest evidence in support of intercalation is the observed chiral discrimination. The Δ enantiomer, a right-handed propeller-like structure, displays a greater affinity than Λ-(phen)$_3$Ru$^{2+}$ for the right-handed DNA helix. FIG. 14 illustrates the basis for the enantiomeric selectivity. With one phenanthroline ligand intercalated, the two nonintercalated ligands of the Δ isomer fit closely along the right-hand helical groove. The nonintercalated ligands of the Λ enantiomer, in contrast, are repelled sterically by the phosphate backbone of the duplex. The disposition of the left-handed enantiomer is opposed to the right-handed helical groove. The stereoselectivity seen here is in the direction proposed originally for (phen)$_3$Zn$^{2+}$ and supports the assignment of the absolute configurations for the zinc enantiomers. No stereoselectivity is apparent in the association of (phen)$_3$Ru$^{2+}$ with Z-DNA. This left-handed helix does not contain a groove of size and depth comparable to that in B-DNA, and therefore comparable or actually mirror image steric constraints are not expected. Instead the base pairs in the Z-DNA helix are pushed outward toward the solvent, resulting in at most a very wide and shallow major "groove". Hence Z-DNA provides a poor template for this discrimination.

Although it is Δ-(phen)$_3$Ru$^{2+}$ that binds preferentially to B-DNA, the Λ enantiomer does intercalate into the right-handed helix. The ratio of affinities of Δ and Λ isomers for B-DNA is 1.1-1.5, depending upon the method of analysis. Luminescence enhancements and unwinding experiments with supercoiled DNA suggest the Δ isomer to bind 30-50% more strongly. It is interesting that supercoiling does not alter the selectivity. Optical enrichment assays, which can be extremely sensitive and reflect a direct competition between enantiomers for the helix, yield values of 10-30% greater affinity of Δ-(phen)$_3$Ru$^{2+}$ for calf thymus DNA. A more precise determination of relative affinities is difficult because the binding constant of either enantiomer for the helix is low. In fact, then, the enantiomer can bind to the right-handed helix, although the phosphate backbone limits access. The addition of bulky substituents onto the phenanthroline rings, in severly blocking interactions of the left-handed enantiomer with the duplex, is necessary to prevent completely intercalation of the Λ isomer.

These results provide an example of stereospecific interactions with DNA. The stereoselectivity observed is governed by the handedness of the DNA helix. The asymmetric duplex structure serves as a template which discriminates in binding the small molecules on the basis of their chirality. It is interesting that the change in symmetry of the metal complex alone yields a significant difference in its recognition by the helix. The comparison of spectroscopic and binding characteristics of isomers of (phen)$_3$Ru$^{2+}$ has afforded a detailed description of the structural basis for the enantiomeric selectivity observed first for (phen)$_3$Zn$^{2+}$ (15). The difference in biological activities of tris-(phenanthroline)metal enantiomers is, perhaps, also a function of this stereoselectivity.(83) Indeed the interaction of (phen)$_3$Ru$^{2+}$ with DNA illustrates how stereospecificity may be incorporated into the design of drugs that bind to the duplex and provides a means to design reagents that can distinguish the handedness of the DNA helix.(35, 63, 64) Certainly these stereospecific interactions underscore the ability of small intercalating drugs to recognize differences in nucleic acid structure.

II. Tris(4,7-diphenyl-1,10-phenanthroline)ruthenium(II)

The chiral DIP complexes, as shown by the experiments described above serve as specific chemical probes for the handedness of the DNA helix in solution. Spectrophotometrics titrations have shown that, although one RuDIP enantiomer, assigned as Λ-RuDIP, does not bind at all to the B-DNA helix, the bulky asymmetric cation can bind to Z-DNA. Monitoring the binding of this isomer to DNA by any means therefore equivalently assays the helical conformation. The intense metal-to-ligand charge-transfer band in the ruthenium complexes provides a particularly sensitive handle with which to examine the binding, either spectrophotometrically or through its accompanying luminescence.

Striking enantiometic selectivity is found in the interactions of the RuDIP cations with right-handed B-DNA, and this chiral discrimination is consistent with an intercalative model. The changes in the visible spectrum of RuDIP, i.e., the hypochromic shift and luminescence enhancement observed in the presence of duplex DNA parallel in detail those seen in spectra of (phen)$_3$Ru$^{2+}$ as a function of DNA addition. It has been shown that (phen)$_3$Ru$^{2+}$ binds to B-DNA by partial intercalation of the phenanthroline ligand between the base pairs (34, 35). Given that generally the ruthenium-metal-to-ligand charge-transfer transition shows little sensitivity to solvent or environment (84, 85), the close resemblance of properties of RuDIP to (phen)$_3$Ru$^{2+}$ suggests that the cations bind the DNA in a similar fashion. Intercalation of the diphenylphenanthroline ligand between the helix base pairs requires that the phenyl groups rotate into the plane of the phenanthroline ligand. This rotation to a planar structure with minimal steric interactions between nearby hydrogen atoms can be accomplished by legthening the carbon-carbon bond between the phenyl and phenanthroline moieties. Equivalent structural distortions are seen in biphenyl, which is planar in the stacked solid lattice (86). Also, the extremely bulky tetrapyridyl-porphyrin cations, which require extensive distortion, are thought to bind to the DNA duplex by intercalation (87, 88). Importantly, once rotated into the plane of the phenanthroline, the phenyl groups in RuDIP add substantially to the surface area available for overlap with the base pairs as compared with (phen)$_3$Ru$^{2+}$, and therefore greater stability of the bound ruthenium-DNA complex is expected. In fact, binding of RuDIP to DNA assayed by any method becomes evident at 10% of the concentration of (phen)$_3$Ru$^{2+}$, which reflects the increased affinity of RuDIP over (phen)$_3$Ru$^{2+}$ for B-DNA. Perhaps the clearest support for the intercalation model rests in the dramatic enhancement in stereoselectivity observed for RuDIP in comparison with (phen)$_3$Ru$^{2+}$. The phenyl groups, while facilitating intercalation of Δ-RuDIP into the right-handed helix, completely preclude binding by the Λ enantiomer.

Corey-Pauling-Kolton space-filling models of the RuDIP complexes with a B-DNA helix are shown in FIG. 15. The orientations with respect to the helix are indicated in the accompanying sketches. The Δ enantiomer, with one diphenylphenanthroline ligand intercalated, can fit very closely along the helical groove. The two nonintercalating ligands, with a disposition in line with the right-handed helix, abut the helical groove. These close hydrophobic interactions of the nonintercalated ligands are not possible with the mirror-image enantiomer. In contrast, as presented in FIG. 14, if one ligand (not visible) is oriented perpendicular to the helix axis, then the two remaining ligands of the Λ enantiomer are disposed contrary to the right-handed groove. The ruthenium model must therefore be shown in front of the DNA helix in the figure, rather than intercalated, because the interaction of the phenyl groups with the DNA-phosphate backbone at the positions indicated by the arrows completely blocks access. Thus, the stereoselectivity that we see is determined by the steric constraints imposed by the asymmetry in the helix, its handedness.

Just as the helix asymmetry can serve as a template to discriminate between RuDIP enantiomers, differential binding by the enantiomers may be used advantageously in determining the chirality of the helix. Table 3 indicates a general scheme to probe helical conformations using RuDIP cations. Although Λ-RuDIP does not bind to the right-handed B-DNA duplex, spectrophotometric titrations have shown significant binding to Z-DNA and therefore hypochromism of Λ-RuDIP on addition of a test DNA sample may be used as an indication of the Z-conformation. It was particularly interesting to us to find that no stereoselectivity governs binding to the Z-form helix. The bulky cation likely avoids the very narrow helical crevice in the Z-DNA structure, and intercalative binding to the more shallow hydrophobic surface in Z-DNA, the equivalent of the major groove in the B-form, would not be expected to yield any chiral discrimination. Z-DNA does not mirror B-DNA in solution. Instead we predict that a left-handed but more B-like conformation (18, 89, 90) would yield a mirror-image selectivity.

TABLE 3

Scheme for probing DNA conformation with RuDIP enantiomers

| Reactivity | | |
|---|---|---|
| With the Δisomer | With the Λisomer | DNA duplex conformation |
| + | − | Right-handed B-like |
| + | + | Left-handed Z-like or lacking a groove |
| − | − | Unstacked or with base pairs inaccesible |
| − | + | Left-handed B-like |

The chiral tris(diphenylphenanthroline) metal complexes may therefore be used in solution to examine DNA helical conformations: those of naturally occurring sequences, in the presence of drugs, and in protein-bound complexes. Furthermore, the reagents represent a new route for conformation-specific drug design.

III. Cobalt(III) Complexes

The DNA cleavage experiments described above are important in several respects. The photoactivated DNA cleavage reaction with Co(phen)$_3$$^{3+}$ illustrates with a simple inorganic complex the notion of DNA strand scission mediated by a locally generated redox reaction.

Reduction of Co(III) with perhaps concomitant hydroxide oxidation may be responsible for cleavage. With regard to applications, this photoactivated reaction should make possible "footprinting" as a function of time. Most importantly, the differential cleavage of ColE1 DNA by enantiomers of Co(DIP)$_3^{3+}$ represents a clear example of a conformation-specific DNA cleaving molecule. This molecule will be useful in determining regions of Z-DNA conformation within long segments of native DNA. Moreover the high level of recognition of DNA conformation by these chiral inorganic complexes suggests the powerful application of stereospecificity in DNA drug design.

IV. Cleavage Site Mapping

Features unique to the plasmid recognition sites determined above with $\Lambda$-Co(DIP)$_3^{3+}$ were examined. A $\Lambda$-Co(DIP)$_3^{3+}$ is not a sequence-specific reagent and there is no sequence homology evident at these positions in pBR322. Instead $\Lambda$-Co(DIP)$_3^{3+}$ is a *conformation-specific* cleavage agent and it is the common left-handed conformation at these locations that is likely to be recognized by the cobalt complex. Alternating purine-pyrimidine sequences have been shown to adopt the Z-DNA conformation most readily, because alternative residues in Z-DNA have bases in the syn conformation. Inspection of the pBR322 sequence revealed that the $\Lambda$-Co(DIP)$_3^{3+}$ recognition sites included the longest runs of alternating purines and pyrimidines allowing for one base out of alternation. Table 1 shows also the alternating sequences that appear within one standard deviation of each measured recognition site. At positions 1447, 2315, 3265, and 4254 begin respectively 14, 14, 13, and 11 base pair regions with alternating purine and pyrimidine residues having one mistake. These regions correspond essentially to one helical turn in a Z-DNA conformation and are the longest of such conformation homology within the plasmid. Sequences not recognized by $\Lambda$-Co(DIP)$_3^{3+}$ were then considered. There are several other sequences, beginning at 1171, 1533, and 1709, that also constitute 11 base pair segments with one mistake that are not significantly cleaved by $\Lambda$-Co(DIP)$_3^{3+}$, and the longest sequence of alternation in the plasmid with no mistakes, 10 bp beginning at position 2785, is also not cleaved. At this stage it is not known whether the flanking sequences at these sites are affecting Z-DNA formation or $\Lambda$-Co(DIP)$_3^{3+}$ recognition. The sequences within the recognition sites detected do have a range of GC contents. It is interesting that the Z-DNA conformation in pBR322 has been detected at the 1447 site in equally low salt buffers by a completely different route, crosslinking studies (80) with anti-Z-DNA antibodies, which lends confirmation to the Z-form assignment. Thus it is proposed that these four sites of alternating purine-pyrimidine residues adopt the Z-conformation under physiological conditions in native supercoiled pBR322 and are specifically recognized and cleaved by $\Lambda$-Co(DIP)$_3^{3+}$.

Figure 13B:
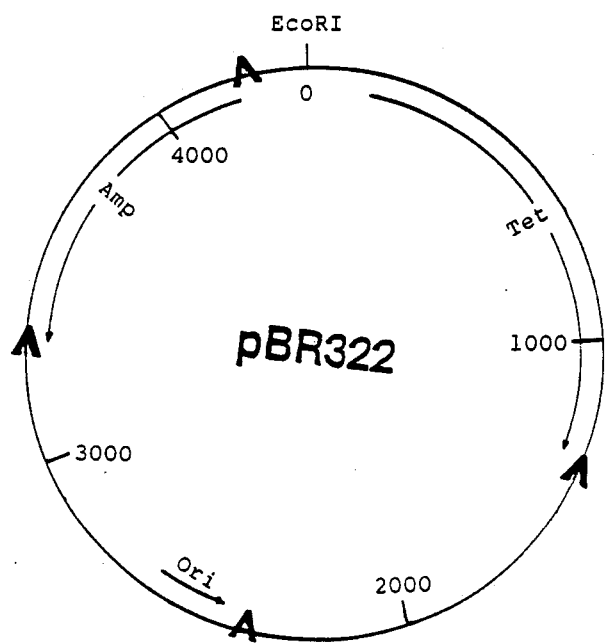

It is interesting, finally, to ask whether these Z-DNA segments share some common biological function in this plasmid. pBR322, assembled from these naturally occurring plasmids, contains three genetically distinct coding regions, the tetracycline resistance genes, the $\beta$-lactamase gene conferring ampicillin resistance, and the origin of replication. FIG. 13B shows the map of these genes in pBR322. It is curious to notice the correspondence in position between the ends of these discrete coding elements and the Z-DNA recognition sites. A single polypeptide in pBR322 appears to be necessary for tetracycline resistance (91). The 3'-end of the region encoding this peptide is thought to be near the AvaI site at 1425 bp; sequences upstream from the tetracycline resistance promotor (which begin at 45 bp) were lost in construction from pSC101. The $\beta$-lactamase gene is defined upstream by the start site at 4201 with the $-35$ consensus region for the promoter ending at 4236, 18 bp away from the Z-form cleavage site (92). The 3'-end of the region encoding $\beta$-lactamase is found at position 3295, which is 22 bp upstream of the Z-form alternating purine-pyrimidine site. Lastly the essential region constituting the origin of replication in pBR322 extends from the RNA/DNA junction at 2536 to position 2360, 32 base pairs from the weak Z-form site detected with $\Lambda$-Co(DIP)$_3^{3+}$ (65, 93). Thus there appears to be a remarkable correspondence between Z-DNA sites recognized by the cobalt complex and the ends of genetic coding elements. It is tempting to suggest that the Z-DNA conformation might provide a general structural signal or punction mark which demarcates the ends of these genes. Consistent with this idea, the Z-conformation has been shown to provide a poor template for transcriptional activity with *E. coli* RNA polymerase (94). This notion is consistent also with the location of alternating purine-pyrimidine tracts in SV40 DNA enhancer sequences which bind anti-Z-DNA antibodies (30), to the d(GT)$_n$ tracts at the ends of yeast chromosomes (95), and to the alternating purine-pyrimidine long terminal repeats in mouse mammary tumor virus (96). Moreover recent experiments with mung bean nuclease in the malaria parasite Plasmodium have demonstrated that a particular conformation rather than a sequence appears to be shared by gene termination sites (97). These correlations of location with conformation are intriguing and support the notion that DNA polymorphism may be involved in gene expression, that specific sequences may adopt specific local conformation which contain information, and that chromosomal regulation may involve DNA conformation-specific signals.

In sum, the results presented herein indicate that several discrete Z-DNA sites exist under native physiological conditions in pBR322. The positions of these sites mark the ends of genetically distinct coding elements in the plasmid. A cobalt complex of this invention, e.g. $\Lambda$-Co(DIP)$_3^{3+}$ thus provides a photoactivated site-specific cleaving agent that is useful to map these sites and should be helpful in establishing a relationship between the locations of Z-DNA segments and its biological function.

V. Anti-tumor Activity

Complexes of this invention showed high potency against leukemia cells in the previously described screen. These complexes should be useful as anti-tumor agents, and should be active in vivo as well, e.g. in a composition containing a pharmaceutically acceptable carrier.

The results set forth in Table 2, above also indicate a synergistic effect when use of a cobalt complex is combined with ultraviolet radiation. A decrease in the amount of cobalt required for cell death of greater than about 10-fold, and in some cases up to 50-fold has thereby been observed.

Isolation of chromatin showed extensive DNA cleavage. Hence it appears that the complexes can pass into the cell, remain intact therein and interact with DNA as a cellular target.

Since these complexes contain large, planar ligands, selective intercalation is optimized. Individual enantiomers and mixed-ligand complexes should also be useful in this and other embodiments of the invention. The Λ Z-specific enantiomers should be especially useful in anti-tumor compositions and uses.

References (I)
1. Lerman, L. S. J. Mol. Biol. 1961, 3, 18.
2. Berman, H. M.; Young, P. R. Ann. Rev. Biophys. Bioeng. 1981, 10, 87.
3. Gale, E. F.; Cundliffe, E.; Reynolds, P. E.; Richmond, M. H.; Waring, M. "The Molecular Basis of Antibiotic Action"; Wiley: London, 1972; p 173.
4. Waring, M. J. J. Mol. Biol. 1970, 54, 247.
5. Neidle, S. Prog. Med. Chem. 1979, 16, 151.
6. (a) Espejo, R. T.; Lebowitz, J. Anal. Biochem. 1976, 72, 95. (b) Wang, J. C. J. Mol. Biol. 1974, 89, 783.
7. Lippard, S. J. Acc. Chem. Res. 1979, 11, 211.
8. Lippard, S. J.; Bond, P. J.; Wu, K. C.; Bauer, W. R., Science (Washington, D.C.) 1976, 194, 726.
9. (a) Jennette, K. W.; Lippard, S. J.; Vassiliades, G. A.; Bauer, W. R. Proc. Natl. Acad. Sci. U.S.A. 1974, 71, 3839. (b) Bond, P. J.; Langridge, R.; Jennette, K. W.; Lippard, S. J. Ibid. 1975, 72, 4285. (c) Barton, J. K.; Lippard, S. J. Biochemistry 1979, 18, 2661. (d) Howe-Grant, M.; Wu, K. C.; Bauer, W. R.; Lippard, S. J. Ibid. 1976, 15, 4339.
10. Wang, A. H.; Nathans, J.; van der Marel, G.; van Boom, J. H.; Rich, A. Nature (London) 1978, 276, 471.
11. Wong, Y. S.; Lippard, S. J. J. Chem. Soc. Chem. Commun. 1977, 824.
12. (a) Hertzberg, R. P.; Dervan, P. B. J. Am. Chem. Soc. 1982, 104, 313. (b) Van Dyke, M. W.; Hertzberg, R. P.; Dervan, P. B. Proc. Natl. Acad. Sci. U.S.A. 1982, 72, 5740. (c) Van Dyke, M. W.; Dervan, P. B. Biochemistry 1983, 22, 2373.
13. (a) Reich, K. A.; Marshall, L. E.; Graham, D. R.; Sigman, D. S. J. Am. Chem. Soc. 1981, 103, 3582. (b) Marshall, L. E.; Graham, D. R.; Reich, K. A.; Sigman, D. S. Biochemistry 1981, 20, 244. (c) Pope, L. E.; Sigman, D. E. Proc. Natl. Acad. Sci. U.S.A. 1984, 81, 3.
14. Cartwright, I. L.; Elgin, S. C. R. Nucleic. Acids Res. 1982, 10, 5835.
15. Barton, J. K.; Dannenberg, J. J.; Raphael, A. L. J. Am. Chem. Soc. 1982, 104, 4967.
16. Wang, A. H.-J., Quigley, G. J., Kolpak, F. J., Crawford, J. L., van Boom, J. H., van der Marel, G. & Rich, A. (1979) Nature (London) 282, 680–686.
17. Pohl, F. M. & Jovin, T. M. (1972) J. Mol. Biol. 67, 375–396.
18. Zacharias, W., Larson, J. E., Klysik, J., Stirdivant, S. M. & Wells, R. D. (1982) J. Biol. Chem. 257, 2775–2782.
19. Behe, M & Felsenfeld, G. (1981) Proc. Natl. Acad. Sci. USA 78, 1619–1623.
20. Santella, R. M., Grunberger, D., Weinstein, E. B. & Rich, A. (1981) Proc. Natl. Acad. Sci. USA 78, 1451–1455.
21. Sage, E. & Leng, M. (1980) Proc. Natl. Acad. Sci. USA 77, 4597–4601.
22. Wells, R. D., Miglietta, J. J., Klysik, J., Larson, J. E., Stirdivant, S. M. & Zacharias, W. (1982) J. Biol. Chem. 257, 10166–10171.
23. Ushay, H. M.; Santella, R. M., Caradonna, J. P., Grunberger, D & Lippard, S. J. (1982) Nucleic Acids Res. 10, 3573–3588.
24. Hanifold, D. B. & Pulleybank, D. E. (1983) Nature (London) 302, 632–634.
25. Nordheim, A. & Rich, A. (1983) Proc. Natl. Acad. Sci. USA 80, 1821–1825.
26. McIntosh, L. P., Greiger, I., Eckstein, F., Zarling, D. A., van de Sande, J. H. & Jovin, T. M. (1983) Nature (London) 304, 83–86.
27. Singleton, C. K., Klysik, J., Stirdivant, S. M. & Wells, R. Dp. (1982) Nature (London) 299, 312–316.
28. Klysik, J., Stirdivant, S. M., Larson, J. E., Hart, P. A. & Wells, R. D. (1981) Nature (London) 290, 672–677.
29. Peck, L. J., Nordheim, A., Rich, A. & Wang, J. C. (1982) Proc. Natl. Acad. Sci. USA 79, 4560–4564.
30. Nordheim, A. & Rich, A. (1983) Nature (London) 303, 674–679.
31. Nordheim, A., Pardue, M. L., Lafer, E. M., Moller, A., Stollar, B. D. & Rich, A. (1981) Nature (London) 294, 417–422.
32. Malfoy, B., Rousseau, M. & Leng, M. (1982) Biochemistry 21, 5463–5467.
33. Miller, A., Gabriels, J. E., Lafer, E. M., Nordheim, A., Rich, A. & Stollar, B. D. (1982) J. Biol. Chem. 257, 12081–12085.
34. Barton, J. K., Danishefsky, A. & Goldberg, J. (1984) J. Am. Chem. Soc., 106, 2172–2176.
35. Barton, J. K. (1983) J. Biomol. Struct. Dyn. 1, 621–632.
36. Bond, P. J., Langridge, R. J., Jennette, K. W. & Lippard, S. J. (1975) Proc. Natl. Acad. Sci. USA 72, 4825–4829.
37. Watts, R. J. & Crosby, G. A. (1971) J. Am. Chem. Soc. 93, 3184–3188.
38. Lin, C. T., Bottcher, W., Chou, M., Creutz, C. & Sutin, N. (1976) J. Am. Chem. Soc. 98, 6536–6544.
39. (a) Hertzberg, R. P.; Dervan, P. B. J. Am. Chem. Soc. 1982, 104, 313. (b) Schultz, P. G.; Taylor, J. S.; Dervan, P. B. Ibid. 1982, 104, 6861. (c) Schultz, P. G.; Dervan, P. B. Proc. Natl. Acad. Sci. U.S.A. 1983, 80, 6834. (d) Taylor, J. S.; Schultz, P. G.; Dervan, P. B. Tetrahedron 1984, 40, 457.
40. (a) Sigman, D. S.; Graham, D. R.; Marshall, L. E.; Reich, K. A. J. Am. Chem. Soc. 1980, 102, 5419; (b) Biochemistry 1981, 20, 244. (c) Que, B. G.; Downey, K. M.; So, A. G. Ibid. 1980, 19, 5987. (d) Recently a phenanthroline-copper complex was shown to cleave right-handed DNA conformations preferentially. See: Pope, L. A.; Sigman, D. S. Proc. Natl. Acad. Sci. U.S.A. 1984, 81, 3.
41. (a) Van Dyke, M. W. Hertzberg, R. P.; Dervan, P. B. Proc. Natl. Acad. Sci. U.S.A. 1982, 79, 5470. (b) Cartwright, I. L.; Hertzberg, R. P.; Dervan, P. B.; Elgin, S. C. R. Proc. Natl. Acad. Sci. U.S.A. 1983, 80, 3213. (c) Cartwright, I. L.; Elgin, S. C. R. Nucleic Acids res. 1982, 10, 5835. (d) Jessee, B.; Gargiulo, G.: Razvi, R.; Woral, A. Ibid. 1982, 10, 5832. (e) Van Dyke, M. W.; Dervan, P. B. Biochemistry 1983, 22, 2372. (f) Lane, M. J.; Dabrowiak, J. C.; Vournakis, J. N. Proc. Natl. Acad. Sci. U.S.A. 1983, 80, 3260.
42. (a) "Bleomycin: Chemical, Biochemical and Biological Aspects"; Hecht, S. M., Ed.; Springer-Verlag: New York, 1979. (b) Sausville, E. A.; Peisach, J.; Horwitz, S. B. Biochemistry 1978, 17, 2740. (c) Burger, R. M.; Peisach, J.; Horwitz, S. B. Life Sci. 1981, 28, 715. (d) Dabrowiak, J. C. J. Inorg. Biochem. 1980, 13, 317. (e) Lown, J. W.; Sim, S. K. Biochem. Biophys. Res. Commun. 1977, 77, 1150.
43. Cone, R.; Hasan, S. K.; Lown, J. W.; Morgan, A. R. Can J. Biochem. 1976, 54, 219.
44. Cobalt (III) polyamine complexes generally undergo photoreduction reactions. See: (a) Adamson, A. W. Coord. Chem. Rev. 1968, 3, 169. (b) Balzani, V.; Maggi, L.; Manfrin, M. F.; Bolletta, F. Ibid. 1975, 15, 321. (c) Adamson, A. W. Pure Appl. Chem. 1979, 51, 313.
45. (a) Sutin, N.; Cruetz, C. Pure Appl. Chem. 1980, 52, 2717. (b) Balanzi, V.; Moggi, L.; Manfrin, M. F.; Bolletta, F.; Laurence, G. S. Coord. Chem. Rev. 1975, 15, 321.
46. (a) Hagar, G. D.; Crosby, G. A.; J. Am. Chem. Soc. 1975, 97, 7031. (b) Hagar, G. D.; Watts, R. J. Crosby, G. A. Ibid. 1975, 97, 7037. (c) Elfring, W. H. Jr.; Crosby, G. A. Ibid. 1981, 103, 2683.
47. Circular dichroic spectra of $Zn(phen)_3^{2+}$, optically enriched by dialysis against DNA (15), show that, while the complex does not racemize instantaneously in aqueous solution, loss of optical activity does occur over a period of days. (Barton, J. K.; Dannenberg, J. J.; Raphael, A. L., to be submitted for publication.) Enantiomers have not however been isolated in pure form. See also: Pfeiffer, P.; Nakatsuka, Y. Ber. Dtsch. Chem. Ges. B 1933, 66B, 415.
48. Brandt, W. W.; Dwyer, F. P.; Gyarfas, E. C. Chem. Rev. 1954, 54, 959 and references therein.
49. Gillard, R. D.; Hill, R. E. E. J. Chem. Soc., Dalton Trans. 1974, 1217.
50. McCaffery, A. J.; Mason, S. F.; Norman, B. J. J. Chem. Soc. A 1969, 1428.
51. Yamagishi, A. J. Chem. Soc., Chem. Commun. 1983, 572.
52. J. K. Barton, L. A. Basile, and A. Danishefsky, Proc. Natl. Acad. Sci. USA, 1984, 81, 1961–1965.
53. Cagle, F. W. Jr., Acta Cryst. 1 158(148).
54. Pohl, F., Jovin, T., Baehr, W. & Holbrook, J. (1972) Proc. Natl. Acad. Sci. USA 69, 3805–3809.
55. van de Sande, J. & Jovin, T. (1982) EMBO J. 1, 115–120.
56. Mirau, P. A. and Kearns, D. R. Nuc. Acids Res. 11, 1931 (1983).
57. Miller, O. J., Miller, D., and Barton, J. K. to be submitted.
58. Dolimore, L. S.; Gillard, R. D. J. Chem. Soc., Dalton Trans. 1973, 933.
59. The low spin $d^6$ octahedral cobalt(III) complexes are kinetically inert to racemization. See: (a) Ellis, P.; Wilkins, R. G.; Williams, M. J. G. J. Chem. Soc. Chem. Commun. 1957, 4456. (b) Yamamoto, M.; Uwate, Y.; Yamamoto, Y. Inorg. Nucl. Chem. Lett.
60. (a) Rich, A., Nordheim, A., and Want, A. H-J. Ann. Rev. Biochem. 53, 791–846 (1984). (b) Dickerson, R. E., Drew, H. R., Conner, B. N., Wing, R. M., Fratini, A. V. and Kopka, M. L. Science 216, 475–485 (1982) and references therein.
61. (a) Patel, D. J., Kozlowski, S. A., Nordheim, A. and Rich, A. Proc. Natl. Acad. Sci. USA 79, 1413–1417 (1982). (b) Pohl, F. M. and Jovin, T. M. J. Mol. Biol. 67, 375–396 (1972). (c) McIntosh, L. P., Grieger, I., Eckstein, F., Zarling, D. A., van de Sande, J. H., and Jovin, T. M. Nature 304, 83–86 (1983). (d) Haniford, D. B. and Pulleybank, E. D. Nature 302, 632–634 (1983).
62. (a) Lilley, D. M. J. Proc. Natl. Acad. Sci. USA 77, 64468–6472 (1980). (b) Saragosti, S., Cereghini, S. and Yaniv, M. J. Mol. Biol 160, 133–146 (1982). (c) Larsen, A. and Weintraub, H. Cell 29, 609–622 (1982).
63. Barton, J. K., Basile, L. A., Danishefsky, A. and Alexandrescu, A. Proc. Natl. Acad. Sci. USA 81, 1961-1965 (1984).
64. Barton, J. K. and Raphael, A. L. J. Am. Chem. Soc. 106, 2466–2468 (1984).
65. (a) Sutcliffe, J. G. Cold Spring Harbor Symp. Quant. Biol. 43, 77–90 (1979). (b) Sutcliffe, J. G. Proc. Natl. Acad. Sci. USA 75, 3737–3741 (1978).
66. Barton, J. K. & Lippard, S. J. (1979) Biochemistry 12, 2661-2668.
67. Reichman, M. E., Rice, S. A., Thomas, C. A. & Doty, P. J. (1954) J. Am. Chem. Soc. 76, 3047–3053.
68. Wells, R. D., Larson, J. E., Grant, R. C., Shortle, B. E. & Cantor, C. R. (1970) J. Mol. Biol. 54, 465–497.
69. Fisher, G. A. (1958) Ann. N.Y. Acad. Sci., 76, 673.
70. LePecq, J. B.; Paoletti, C. (1967) J. Mol. Biol. 27, 87.
71. Scatchard, G., Ann. N.Y. Acad. Sci., 1949, 51, 660.
72. McGhee, J. D.; von Hippel, P. H., J. Mol. Biol., 1974, 86, 469.
73. Howe-Grant, M.; Lippard, S. J., Biochem., 1979, 18, 5762.
74. Crothers, D. M., Biopolymers, 1968, 6, 575.
75. Pohl, F., Jovin, T., Baehr, W. & Holbrook, J. (1972) Proc. Natl. Acad. Sci. USA 69, 3805–3809.
76. van de Sande, J. and Jovin, T. (1982) EMBO J. 1, 115–120.
77. Wang. A. H. J., Fujii, S., van Boom, J. H. and Rich, A. (1982) Proc. Natl. Acad. Sci. USA 79, 3968–3972.
78. (a) Tullius, T. D. et al., ACS Symp. Ser., 1983, No. 209, 51. (b) Cohen et al., Science, 1970, 203, 1014.
79. Peck, L. J.; Wang, J. C. Ibid. 1983, 80, 6206. We thank Professor C. Cantor for a gift of this plasmid.
80. (a) Azorin, F.; Nordheim, A.; Rich, A. EMBO J. 1983, 2, 649. (b) Nordheim, A.; Lafer, E. M.; Peck, L. J.; Wang, J. C.; Stollar, B. D.; Rich, A. Cell 1982, 31, 309. (c) Rich, A.; Nordheim, A.; Azorin, F. J. Biomol. Struct. Dyn. 1983, 1, 1.
81. Stirdivant, S. M., Klysik, J. and Wells, R. D. J. Biol. Chem. 257, 10159–10165 (1982).
82. Hauenstein, B. L., Jr.; Dressick, W. J.; Buell, S. L.; Demas, J. N.; DeGraff, B. A. J. Am. Chem. Soc. 1983, 105, 4251.
83. Dwyer, F. P. et al., Nature, 1952, 170, 190.
84. Watts, R. J. and Crosby, G. A. (1971) J. Am. Chem. Soc. 93, 3184–3188.
85. Lin, C. T., Bottcher, W., Chou, M., Creutz, C. and Sutin, N. (1976) J. Am. Chem. Soc. 98, 6536–6544.
86. Cagle, F. W., Jr. (1984) Acta Crystallogr. 1, 158–159.
87. Fiel, R. J., Howard, J. C., Mark, E. H. & Gupta, N. D. (1979) Nucleic Acids. Res. 6, 3093–3118.
88. Pasternack, R. F., Gibbs, E. J. & Villafranca, J. J. (1982) Biochemistry 22, 2406–2414.
89. Arnott, S., Chandrasekaran, R., Birdsall, D. L., Leslie, A. G. W. & Ratliff, R. L. (1980) Nature (London) 283, 743–745.
90. Gupta, G., Bansal, M. & Sasisekharan, V. (1980) Proc. Natl. Acad. Sci. USA 77, 6486–6490.
91. Backman, K. and Boyer, H. W. Gene 26, 197–203 (1983).
92. Brosius, J., Cate, R. L., and Permutter, A. P. J. Biol. Chem. 257, 9205–9210 (1982).
93. Tomizawa, J. I., Ohmori, H. and Bird, R. E. Proc. Natl. Acad. Sci. USA 74, 1865–1869 (1977).

94. Butzow, J. J., Shin, Y. A., and Eichhorn, G. L. *Biochemistry* 23, 4837–4843 (1984).
95. Walmsley, R. M., Szostak, J. W. Petes, T. D. *Nature* 302, 84–86 (1983).
96. See, for example Kennedy, N., Knedlitschek, G., Groner, B., Hynes, N. E., Herrlich, P., Michalides, R., and van Ooyen, A. J. J. *Nature* 295, 622–624 (1982).
97. McCutchan, T. F., Hansen, J. L., Dane, J. B. and Mullins, J. A. *Science* 225, 625–628 (1984).
98. Dwyer, F. P.; Reid, I. K.; Shulman, A.; Laycock, G. M. and Dixon, S., Aust. J. Exp. Biol. Med. Sci., 1969, 47, 203; Dwyer, F. P.; Mayhew, E.; Roe, E. M. F.; and Shulman, A., Brit. J. Cancer, 1965, 19, 195; Shulman, A. and White, D. O., Chem. Biol. Inter., 1973, 6, 407; Shulman, A. and Laycock, G. M., Chem. Biol. Inter., 1977, 16, 89.

What is claimed is:

1. A method for detecting in a sample the presence of double-stranded DNA comprising contacting the sample with a complex of the formula $(R)_3$—Co (III), wherein R comprises 1,10-phenanthroline or a substituted derivative thereof and R is bound to Co(III) by a coordination bond, the contacting being effected under conditions such that the complex binds to double-stranded DNA present in the sample by intercalation and thereby labels the double-stranded DNA with the complex, detecting DNA labeled with the complex, and thereby detecting the presence of double-stranded DNA in the sample.

2. A method of claim 1, wherein the substituted derivative of 1,10-phenanthroline comprises 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline, or 3,8-dispermine-1,10-phenanthroline.

3. A method for detecting in a sample the presence of double-stranded Z-DNA which comprises contacting the sample with the lambda enantiomer of a complex having the formula $(R)_3$—M, wherein R comprises 1,10-phenanthroline or a substituted derivative thereof, M comprises ruthenium (II) or cobalt (III) and R is bound to M by a coordination bond, the contacting being effected under conditions such that the complex binds to double-stranded Z-DNA present in the sample by intercalation and thereby labels the double-stranded Z-DNA with the lambda enantiomer of the complex, detecting Z-DNA labeled with the lambda enantiomer of the complex, and thereby detecting the presence of double-stranded Z-DNA in the sample.

4. A method of claim 3 wherein M is ruthenium(II).

5. A method of claim 3, wherein M is cobalt(III).

6. A method of claim 3, wherein the substituted derivative of 1,10-phenanthroline comprises 4,7-diamino-1,10-phenanthroline; 3,8-diamino-1,10-phenanthroline; 4,7-diethylenediamine-1,10-phenanthroline; 3,8-diethylenediamine-1,10-phenanthroline; 4,7-dihydroxyl-1,10-phenanthroline; 3,8-dihydroxyl-1,10-phenanthroline; 4,7-dinitro-1,10-phenanthroline; 3,8-dinitro-1,10-phenanthroline; 4,7-diphenyl-1,10-phenanthroline; 3,8-diphenyl-1,10-phenanthroline; 4,7-dispermine-1,10-phenanthroline, or 3,8-dispermine-1,10-phenanthroline.

7. A method for nicking double-stranded DNA by effecting breakage of at least one phosphodiester bond along the DNA which comprises contacting the DNA with a coordination complex or salt thereof having the formula $(R)_3$—Co (III), wherein R comprises 1,10-phenanthroline or a substituted derivative thereof and R is bound to Co by a coordination bond, under conditions such that the complex binds to the DNA by intercalation to form an adduct and irradiating the adduct so formed with ultraviolet radiation of a wavelength which is absorbed by the ligand bands of the complex so as to nick the DNA at the site(s) of intercalation.

8. A method for cleaving double-stranded DNA which comprises nicking the DNA according to claim 7 and treating the nicked DNA so produced with an enzyme which is not deactivated in the presence of the complex used for DNA nicking and capable of cleaving single-stranded DNA so as to cleave the nicked DNA at the site of the nick(s).

9. A method for selectively nicking Z-DNA, present in DNA comprising Z-DNA and other forms of DNA, by effecting breakage of at least one phosphodiester bond along the Z-DNA which comprises contacting the DNA containing the Z-DNA with a $\Lambda$ isomer of a coordination complex or salt thereof having the formula $(R)_3$—CO(III), wherein R comprises 1,10-phenanthroline or a substituted derivative thereof and R is bound to Co by a coordination bond, under conditions such that the $\Lambda$ isomer binds to the DNA by intercalation to form an adduct and irradiating the adduct so formed with ultraviolet radiation of a wavelength which is absorbed by the ligand bands of the $\Lambda$ isomer so as to nick the DNA at the site(s) of intercalation.

10. A method for selectively cleaving double-stranded Z-DNA, present in DNA comprising Z-DNA and other forms of DNA, which comprises nicking the Z-DNA according to claim 9 and treating the nicked DNA so produced with an enzyme which is not deactivated in the presence of the complex used for DNA nicking and capable of cleaving single-stranded DNA so as to cleave the nicked DNA at the site of the nick(s).

* * * * *